US008816076B2

(12) United States Patent
Beard et al.

(10) Patent No.: US 8,816,076 B2
(45) Date of Patent: Aug. 26, 2014

(54) ARYL UREA DERIVATIVES AS N-FORMYL PEPTIDE RECEPTOR LIKE-1 (FPRL-1) RECEPTOR MODULATORS

(71) Applicant: Allergan, Inc., Irvine, CA (US)

(72) Inventors: Richard L. Beard, Newport Beach, CA (US); Tien T. Duong, Rancho Santa Margarita, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/966,558

(22) Filed: Aug. 14, 2013

(65) Prior Publication Data

US 2013/0331570 A1 Dec. 12, 2013

Related U.S. Application Data

(62) Division of application No. 13/668,835, filed on Nov. 5, 2012, now Pat. No. 8,541,577.

(60) Provisional application No. 61/558,121, filed on Nov. 10, 2011.

(51) Int. Cl.
*C07C 275/30* (2006.01)
*C07C 323/44* (2006.01)
*C07D 213/55* (2006.01)
*C07D 213/75* (2006.01)
*C07D 209/20* (2006.01)
*C07D 239/84* (2006.01)

(52) U.S. Cl.
CPC ............. *C07C 275/30* (2013.01); *C07C 323/44* (2013.01); *C07D 213/55* (2013.01); *C07D 239/84* (2013.01); *C07D 209/20* (2013.01); *C07D 213/75* (2013.01)
USPC ........... 544/292; 546/306; 546/332; 548/496; 562/439; 562/426; 564/53; 564/54

(58) Field of Classification Search
USPC ........... 544/292; 562/439, 426; 546/332, 306; 548/496; 564/53, 54
See application file for complete search history.

(56) References Cited

U.S. PATENT DOCUMENTS 6,353,099 B1 * 3/2002 DeLaszlo et al. ............. 540/490
2004/0038858 A1 * 2/2004 Dorsch et al. ..................... 514/1

FOREIGN PATENT DOCUMENTS

| JP | 63232846 | 9/1988 |
| WO | 01-14328 | 3/2001 |
| WO | 2011-073918 | 6/2011 |
| WO | WO 2011094890 A1 * | 8/2011 |

OTHER PUBLICATIONS

Cross, L.C. et al, Rules for the Nomenclature of Organic Chemistry, Section E: Stereochemistry, Pure & Appl. Chem., 1976, 11-30, 45.
Migeotte, Isabelle et al., Formyl peptide receptors: A promiscuous subfamily of G protein-coupled receptors controlling immune responses, Cytokine & Growth Factor Reviews, 2006, 501-519, 17, US.
Perretti, Mauro et al, Therapeutic Anti-Inflammatory Potential of Formyl-Peptide Receptor Agonists, Pharmacology & Research, 2010, 175-188, 127.
Stahl, Heinrich et al, Handbook of Pharmaceutical Salts, Verlag Helvetica Chimica Acta—Zurich, 2002, 329-345.
Ogura et al. JP 63232846A, published Sep. 28, 1988, (English Abstract).

\* cited by examiner

*Primary Examiner* — Samantha Shterengarts
*Assistant Examiner* — Amanda L Aguirre
(74) *Attorney, Agent, or Firm* — Doina G. Ene

(57) ABSTRACT

The present invention relates to novel aryl urea derivatives, processes for preparing them, pharmaceutical compositions containing them and their use as pharmaceuticals as modulators of the N-formyl peptide receptor like-1 (FPRL-1) receptor.

8 Claims, No Drawings

ARYL UREA DERIVATIVES AS N-FORMYL PEPTIDE RECEPTOR LIKE-1 (FPRL-1) RECEPTOR MODULATORS

RELATED APPLICATIONS

This application is a divisional application of U.S. Non-Provisional patent application Ser. No. 13/668,835, filed Nov. 5, 2012, which claims the benefit of U.S. Provisional Application Ser. No. 61/558,121, filed on Nov. 10, 2011, all of which are incorporated here by reference in their entirety.

FIELD OF THE INVENTION

The present invention relates to novel aryl urea derivatives, processes for preparing them, pharmaceutical compositions containing them and their use as pharmaceuticals as modulators of the N-formyl peptide receptor like-1 (FPRL-1) receptor. The invention relates specifically to the use of these compounds and their pharmaceutical compositions to treat disorders associated with the N-formyl peptide receptor like-1 (FPRL-1) receptor modulation.

BACKGROUND OF THE INVENTION

The N-formyl peptide receptor like-1 (FPRL-1) receptor, also known as the N-formyl peptide receptor 2 (FPR2), is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide human, anti-inflammatory eicosanoid lipoxin A4 (LXA4) and glucocotricoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists. Parmentier, Marc et al. Cytokine & Growth Factor Reviews 17 (2006) 501-519.

Activation of FPRL-1 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner. In addition, FPRL-1 has been shown to inhibit NK cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

A group of novel aryl urea derivatives which are potent and selective FPRL-1 modulators has been discovered. As such, the compounds described herein are useful in treating a wide variety of disorders associated with modulation of FPRL-1 receptor. The term "modulator" as used herein, includes but is not limited to: receptor agonist, antagonist, inverse agonist, inverse antagonist, partial agonist, partial antagonist.

This invention describes compounds of Formulae I, II and III, which have FPRL-1 receptor biological activity. The compounds in accordance with the present invention are thus of use in medicine, for example in the treatment of humans with diseases and conditions that are alleviated by FPRL-1 modulation.

In one aspect, the invention provides a compound represented by Formula I or enantiomers, diastereoisomers, tautomers, hydrates, solvates, zwitterions or a pharmaceutically acceptable salt thereof:

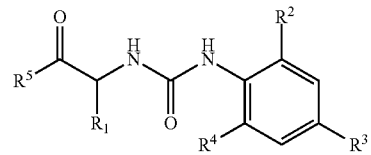

Formula I wherein:

$R^1$ is sec-butyl, $C_{6-10}$ aryl, —$CH_2$—($C_{6-10}$)aryl, —$CH_2$-heterocycle, $C_{4-8}$ cycloalkyl or $C_{3-8}$ cycloalkenyl or heterocycle;

$R^2$ is halogen or methyl;

$R^3$ is halogen;

$R^4$ is H, methyl or halogen;

$R^5$ is $OR^6$;

$R^6$ is H or $C_{2-4}$ alkyl; and compounds

2-[({[4-(methylthio)phenyl]amino}carbonyl)amino]-3-phenylpropanoic acid;

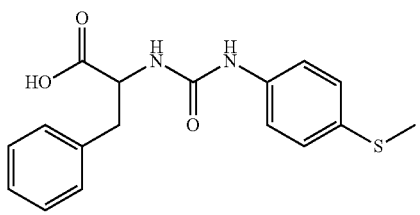 [SMILES: CSc1ccc(NC(=O)NC(Cc2ccccc2)C(=O)O)cc1]

2-({[(4-bromophenyl)amino]carbonyl}amino)-3-pyridin-2-ylpropanoic acid;

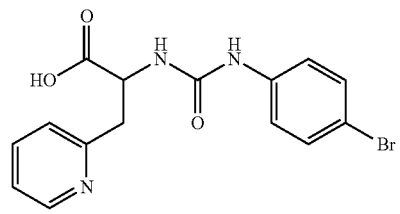 [SMILES: O=C(Nc1ccc(Br)cc1)NC(Cc1ccccn1)C(=O)O]

(2S)-2-[({[4-(methylthio)phenyl]amino}carbonyl)amino]-3-phenylpropanoic acid;

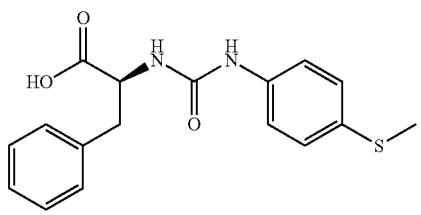 [SMILES: CSc1ccc(NC(=O)N[C@@H](Cc2ccccc2)C(=O)O)cc1]

with provisio that the compound of Formula I is not of structures

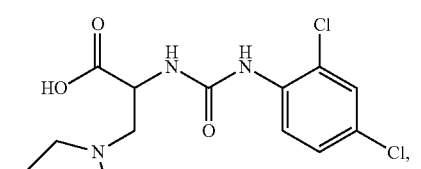

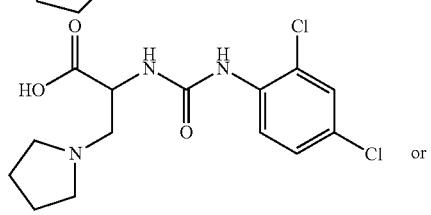

or

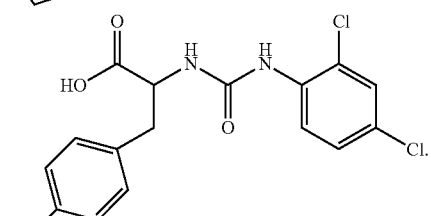

In another aspect, the invention provides a compound represented by Formula II or enantiomers, diastereoisomers, tautomers, hydrates, solvates, zwitterions or a pharmaceutically acceptable salt thereof:

Formula II

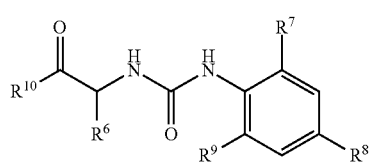

wherein:

$R^6$ is —CH$_2$—(C$_{6-10}$)aryl or —CH$_2$-heterocycle;

$R^7$ is H, F or methyl;

$R^8$ is Br or F;

$R^9$ is H, F or methyl;

$R^{10}$ is OH or NH$_2$; and including the following structures or enantiomers, diastereoisomers, tautomers, hydrates, solvates, zwitterions or a pharmaceutically acceptable salt thereof:

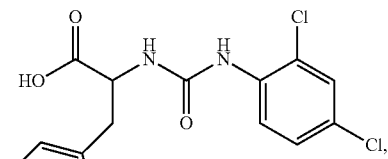

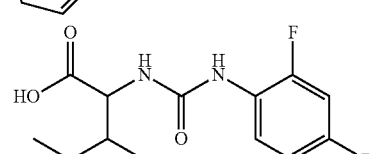

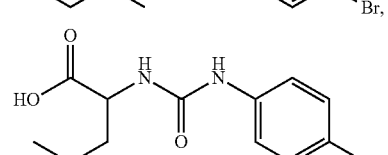

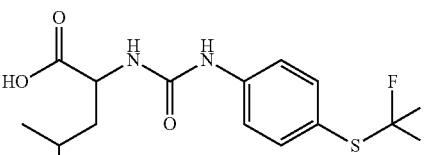

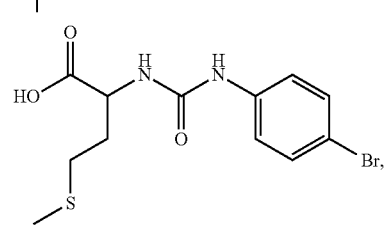

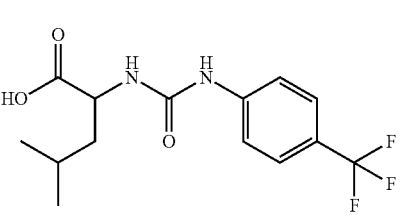

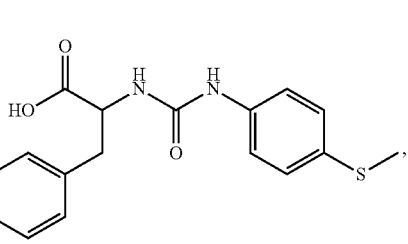

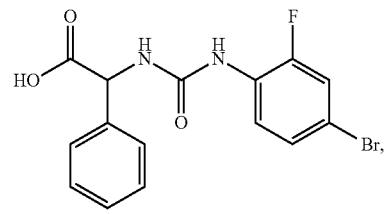

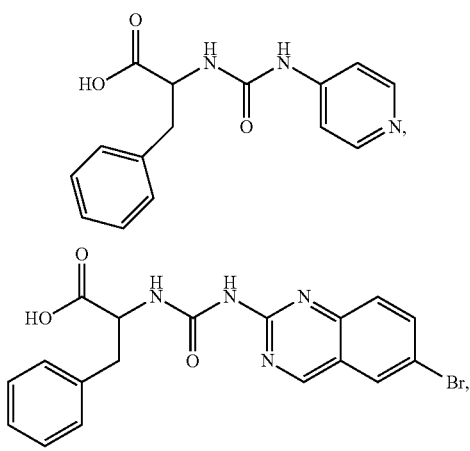

and excluding structures or enantiomers, diastereoisomers, tautomers, hydrates, solvates, zwitterions or a pharmaceutically acceptable salt thereof:

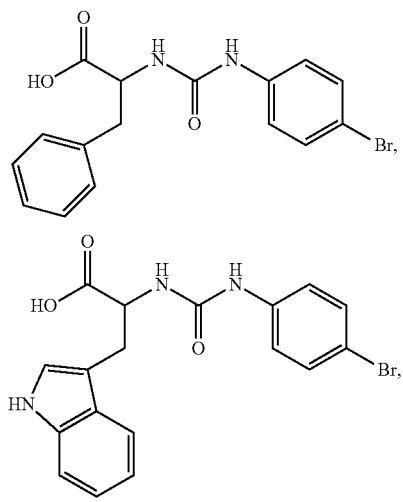

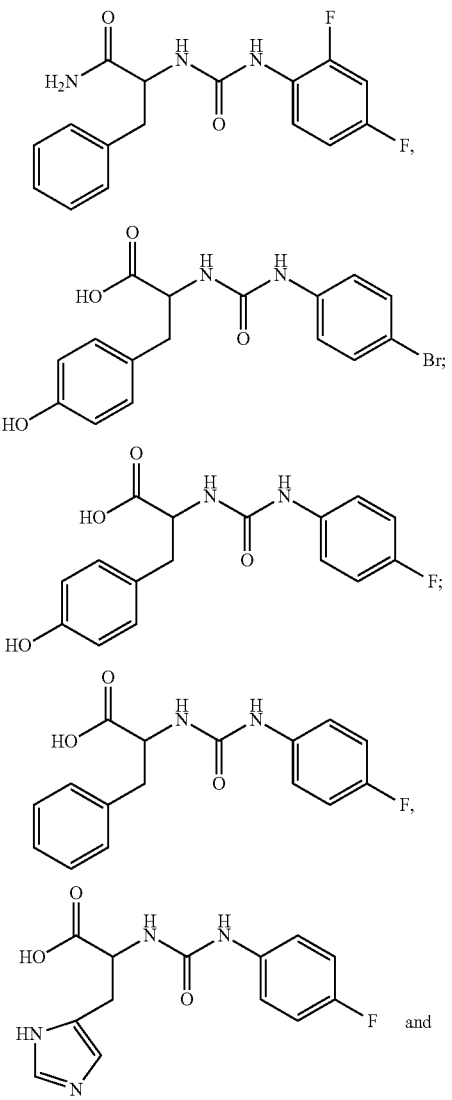

In another aspect, the invention provides a compound represented by Formula II, wherein:

$R^6$ is —CH$_2$—(C$_{6-10}$)aryl;

$R^7$ is H, F or methyl;

$R^8$ is Br or F;

$R^9$ is H, F or methyl;

$R^{10}$ is OH or NH$_2$; and including the following structures or enantiomers, diastereoisomers, tautomers, hydrates, solvates, zwitterions or a pharmaceutically acceptable salt thereof:

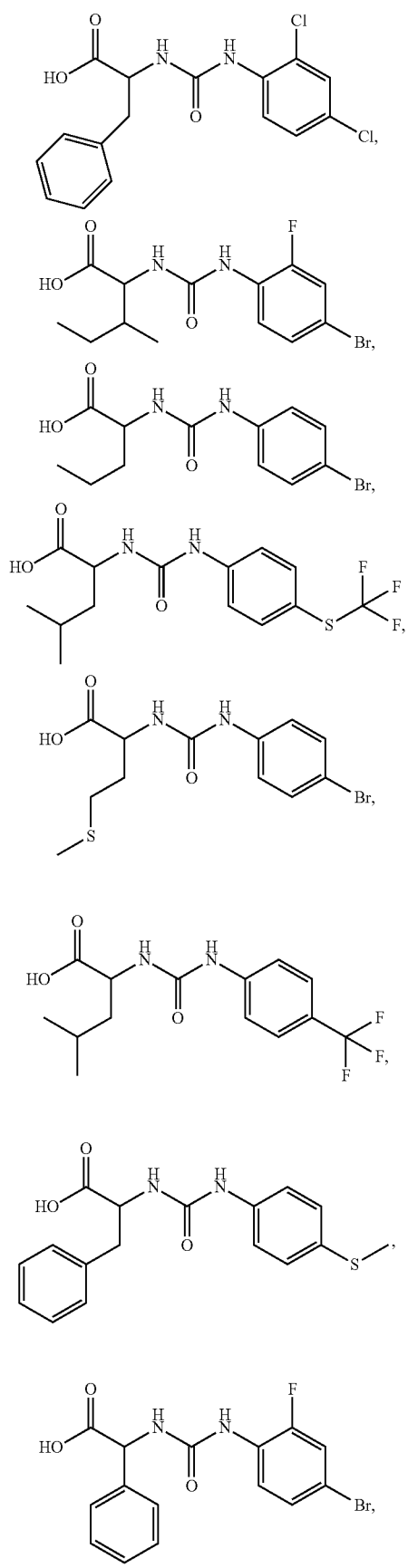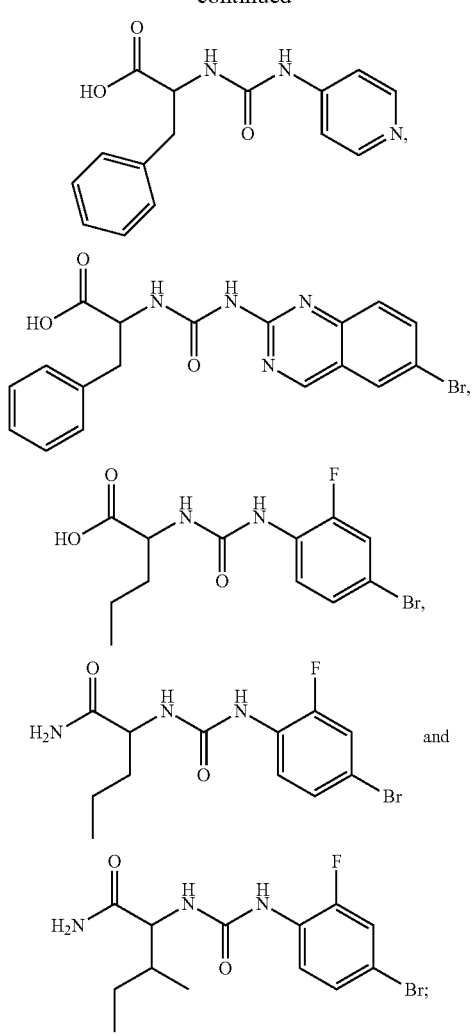
and excluding structures or enantiomers, diastereoisomers, tautomers, hydrates, solvates, zwitterions or a pharmaceutically acceptable salt thereof:
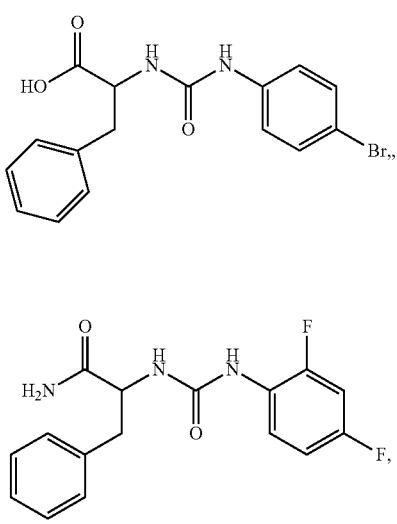

-continued

[Structures of compounds shown]

In another aspect, the invention provides a compound represented by Formula II, wherein:
R⁶ is —CH₂-heterocycle;
R⁷ is H, F or methyl;
R⁸ is Br or F;
R⁹ is H, F or methyl;
R¹⁰ is OH or NH₂; and
including the following structures or enantiomers, diastereoisomers, tautomers, hydrates, solvates, zwitterions or a pharmaceutically acceptable salt thereof:

[Chemical structures continued]

-continued

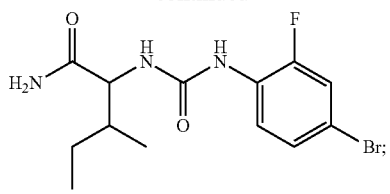

and excluding structures or enantiomers, diastereoisomers, tautomers, hydrates, solvates, zwitterions or a pharmaceutically acceptable salt thereof:

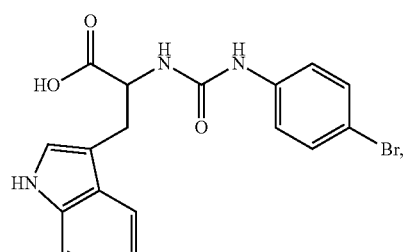

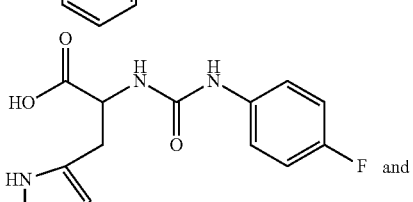

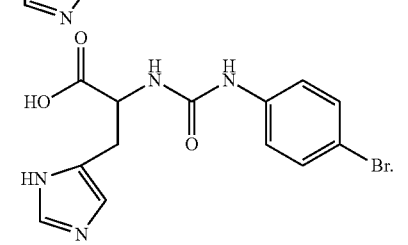

In another aspect, the invention provides a compound represented by Formula II, wherein:

$R^6$ is —CH$_2$—(C$_{6-10}$)aryl or —CH$_2$-heterocycle;
$R^7$ is H, F or methyl;
$R^8$ is Br;
$R^9$ is H, F or methyl;
$R^{10}$ is OH or NH$_2$; and including the following structures or enantiomers, diastereoisomers, tautomers, hydrates, solvates, zwitterions or a pharmaceutically acceptable salt thereof:

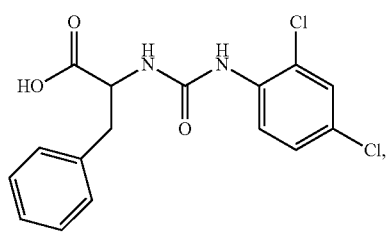

-continued

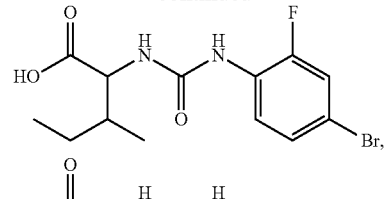

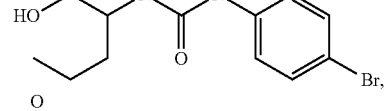

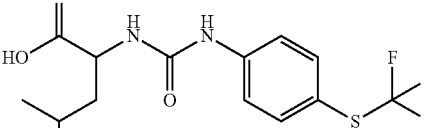

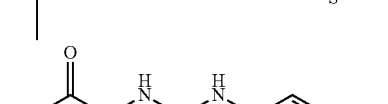

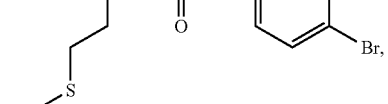

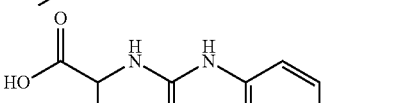

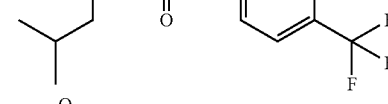

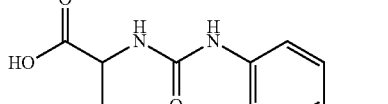

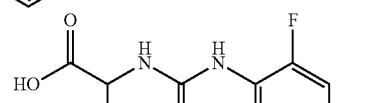

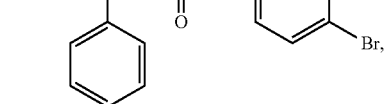

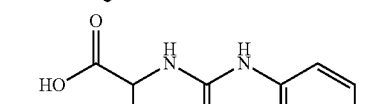

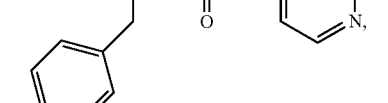

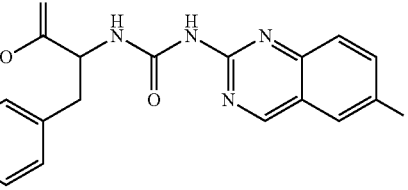

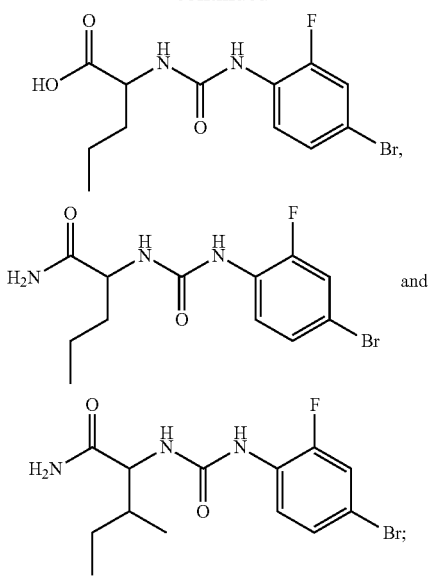

and excluding structures or enantiomers, diastereoisomers, tautomers, hydrates, solvates, zwitterions or a pharmaceutically acceptable salt thereof:

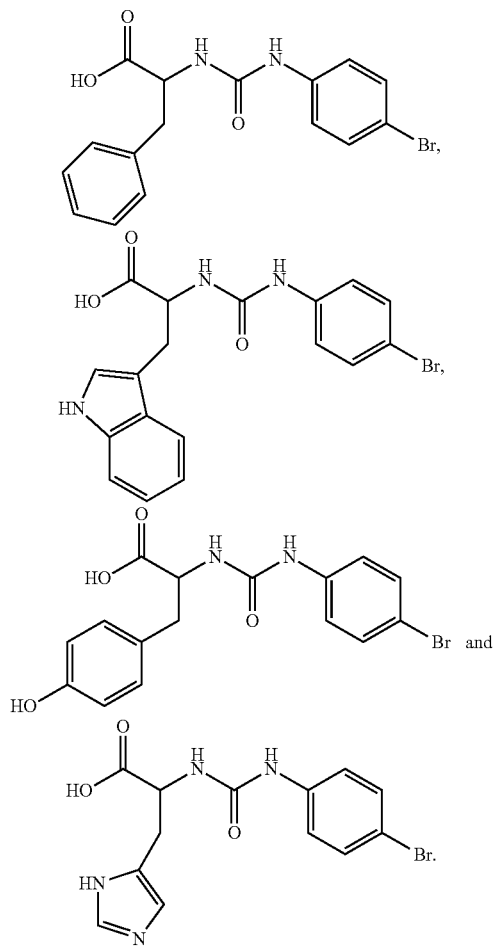

In another aspect, the invention provides a compound represented by Formula II, wherein:

$R^6$ is —$CH_2$—$(C_{6-10})$aryl or —$CH_2$-heterocycle;
$R^7$ is H;
$R^8$ is Br or F;
$R^9$ is H;
$R^{10}$ is OH; and including the following structures or enantiomers, diastereoisomers, tautomers, hydrates, solvates, zwitterions or a pharmaceutically acceptable salt thereof:

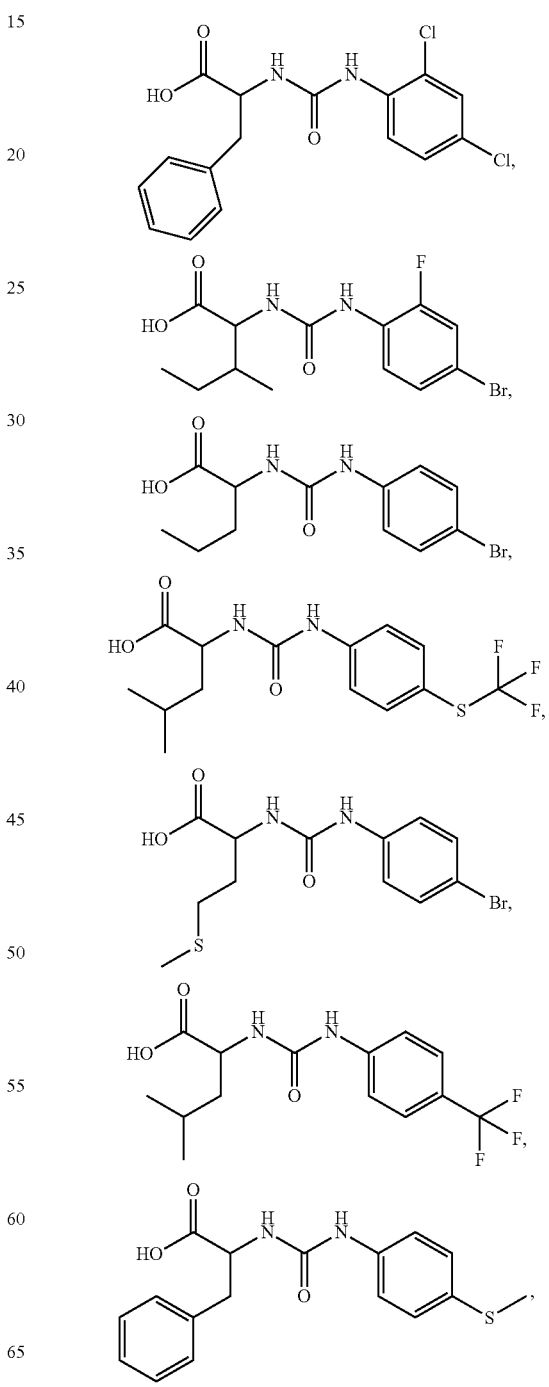

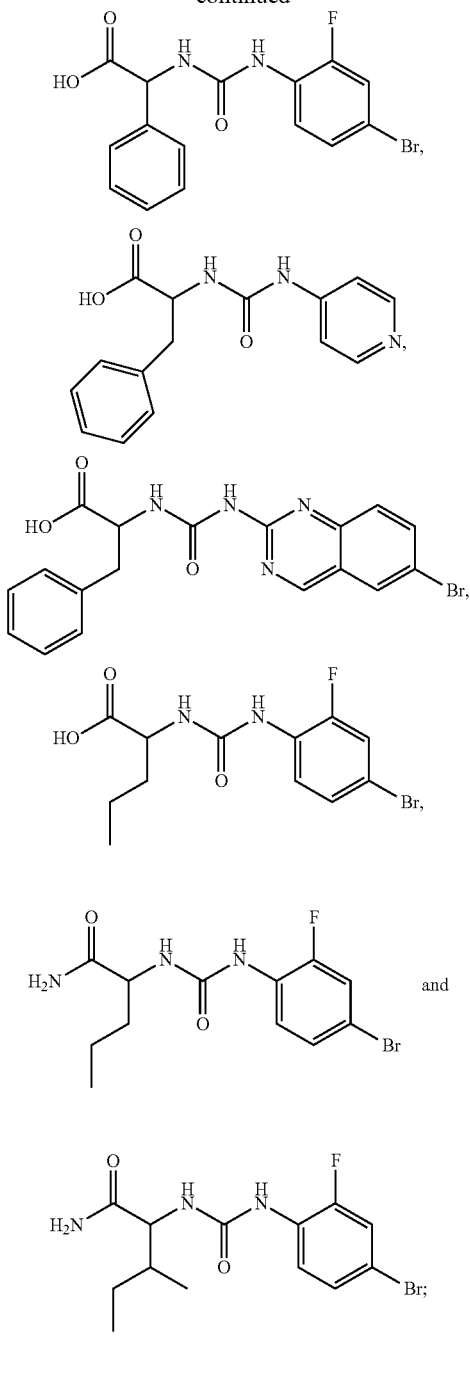
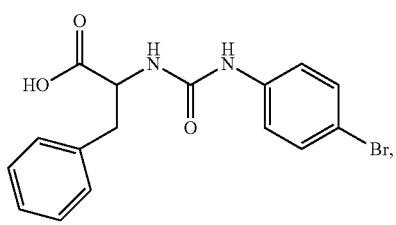

and excluding structures or enantiomers, diastereoisomers, tautomers, hydrates, solvates, zwitterions or a pharmaceutically acceptable salt thereof:

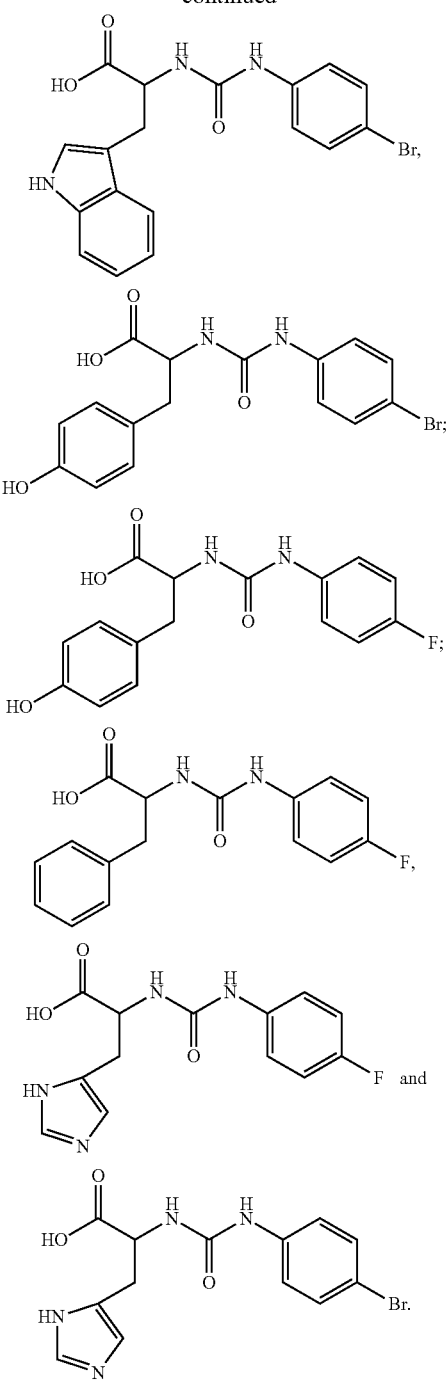

In another aspect, the invention provides a compound represented by Formula II, wherein:

$R^6$ is —$CH_2$—$(C_{6-10})$aryl or —$CH_2$-heterocycle;

$R^7$ is H;

$R^8$ is Br or F;

$R^9$ is H;

$R^{10}$ is $NH_2$; and including the following structures or enantiomers, diastereoisomers, tautomers, hydrates, solvates, zwitterions or a pharmaceutically acceptable salt thereof:

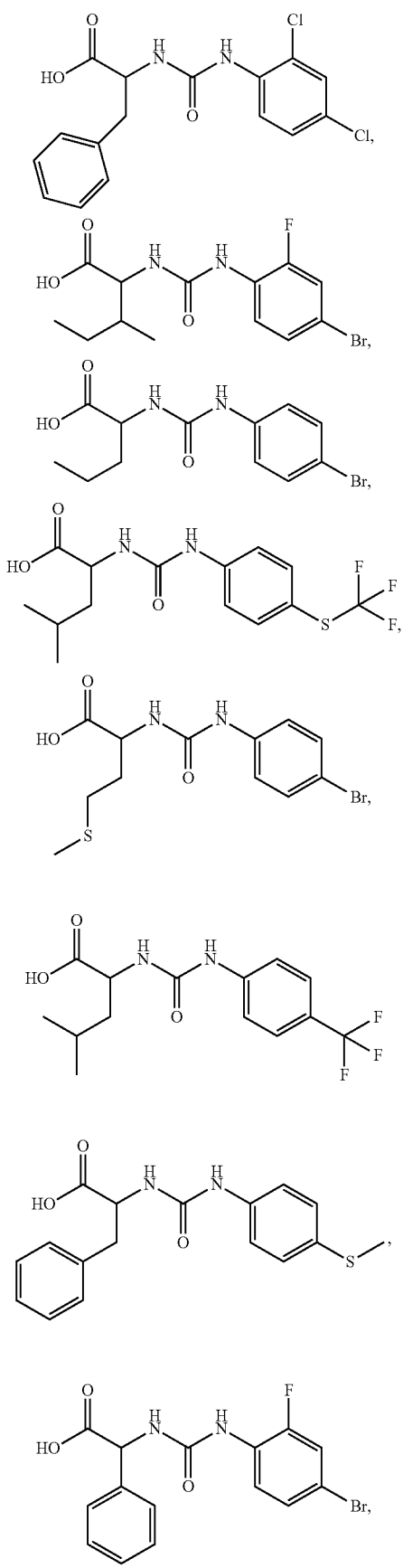
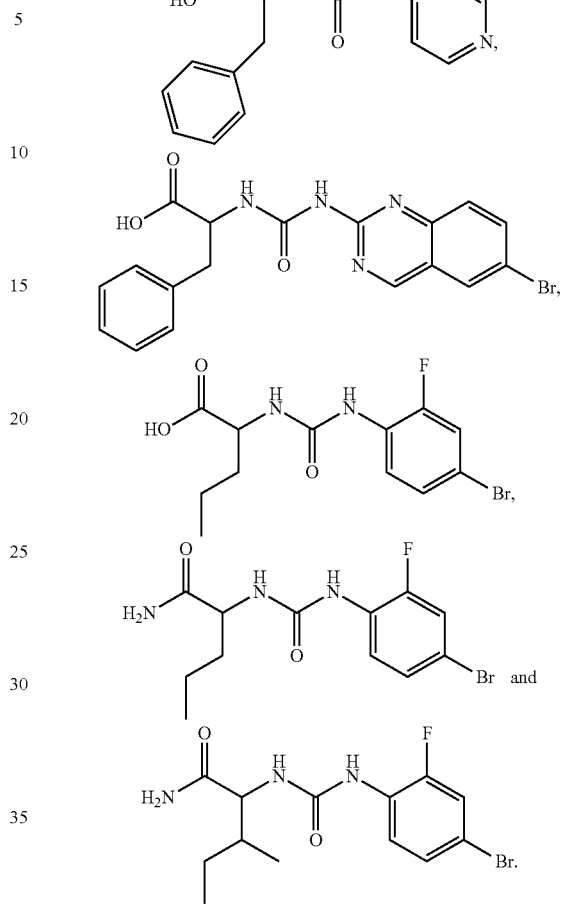
In another aspect, the invention provides a compound represented by Formula II, wherein:
$R^6$ is —$CH_2$—$(C_{6-10})$aryl or —$CH_2$-heterocycle;
$R^7$ is H;
$R^8$ is Br or F;
$R^9$ is H;
$R^{10}$ is OH or $NH_2$; and
including the following structures or enantiomers, diastereoisomers, tautomers, hydrates, solvates, zwitterions or a pharmaceutically acceptable salt thereof:
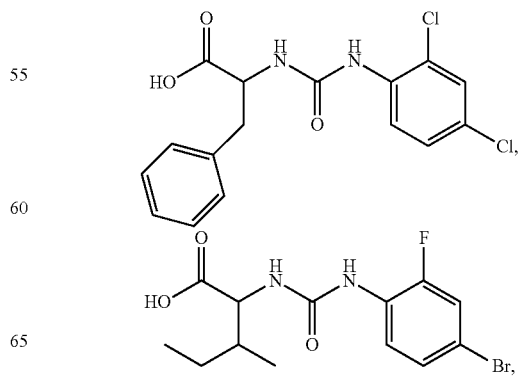

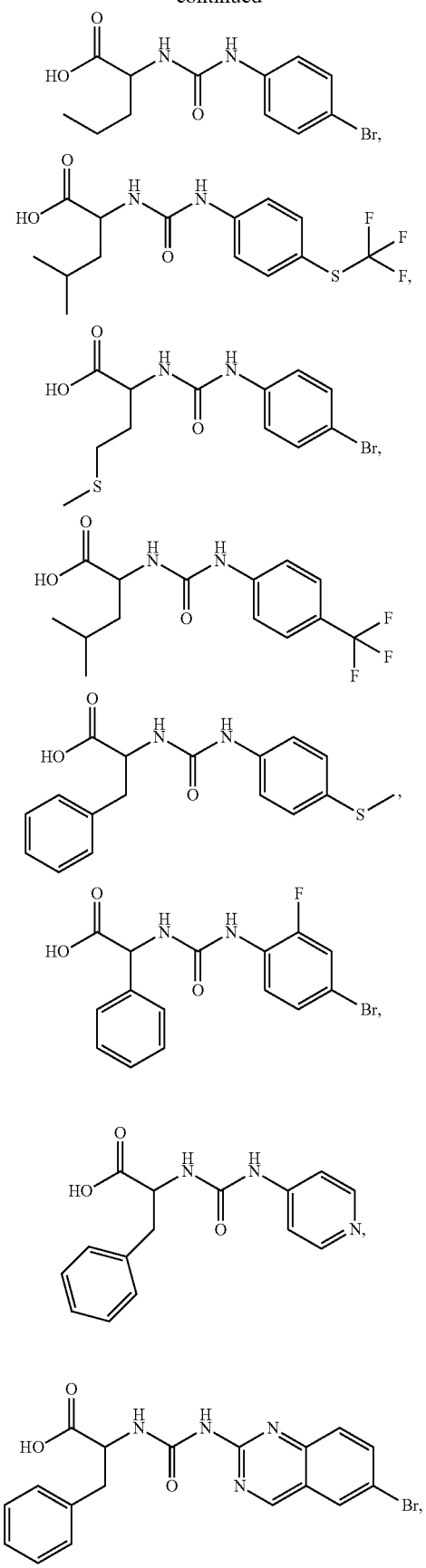
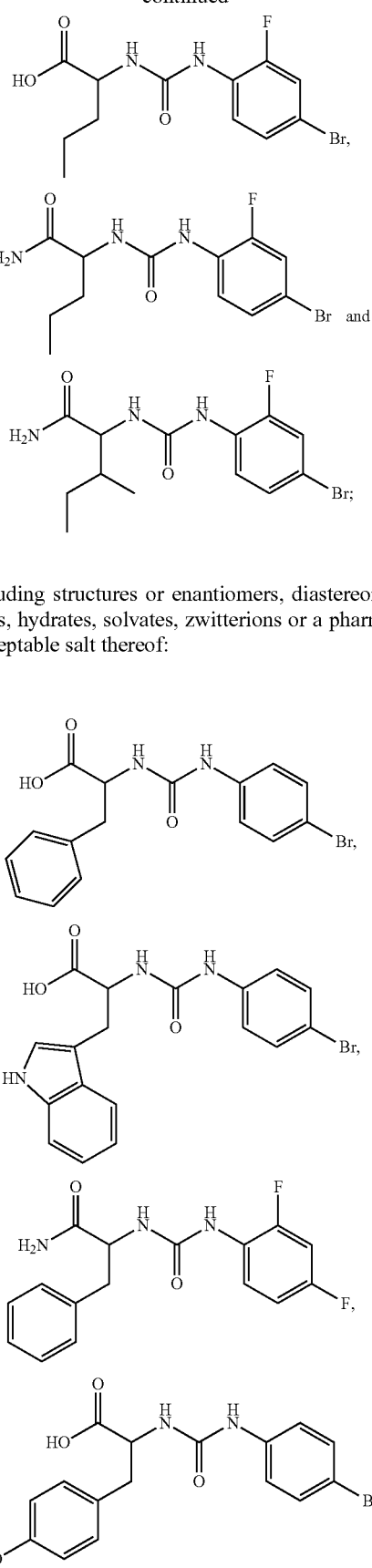
and excluding structures or enantiomers, diastereoisomers, tautomers, hydrates, solvates, zwitterions or a pharmaceutically acceptable salt thereof:

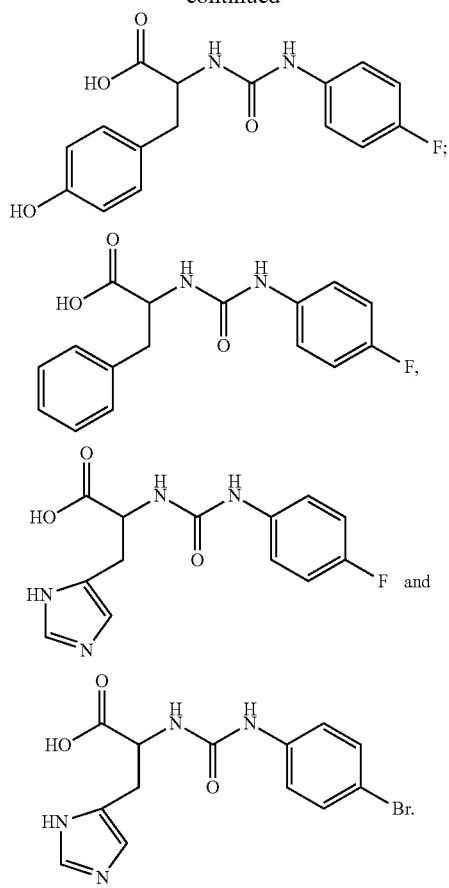
In another aspect, the invention provides a compound represented by structures or enantiomers, diastereoisomers, tautomers, hydrates, solvates, zwitterions or a pharmaceutically acceptable salt thereof:
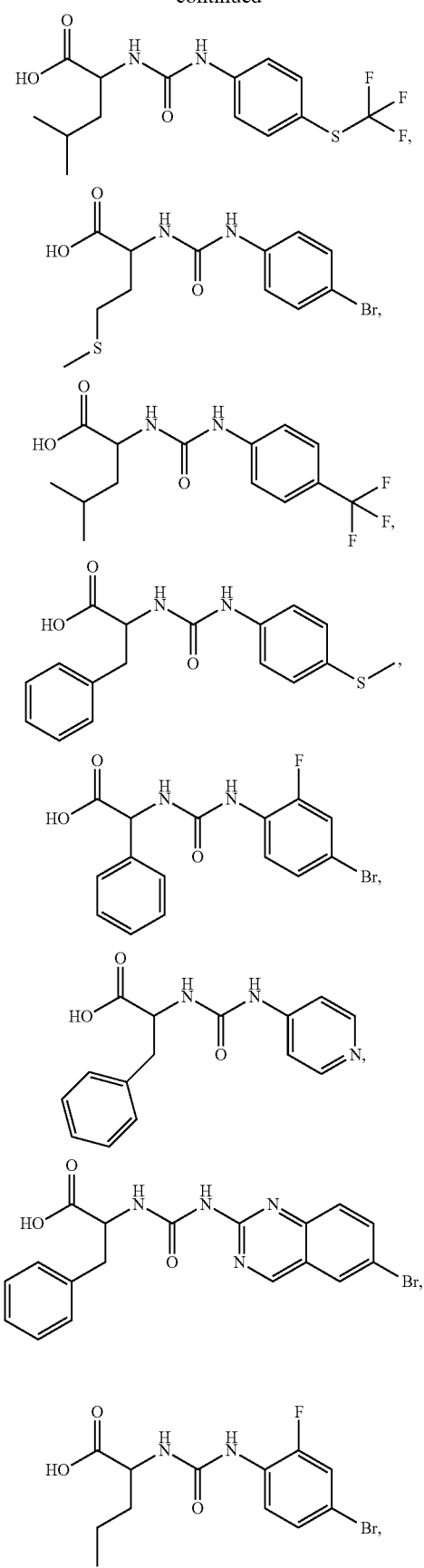

-continued

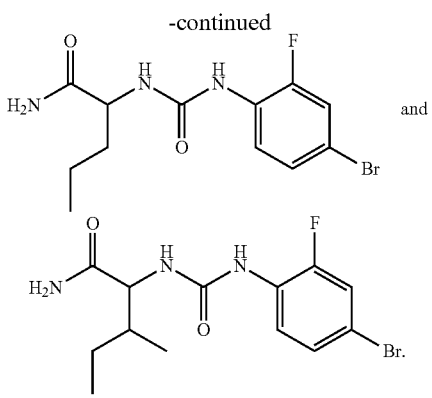

and

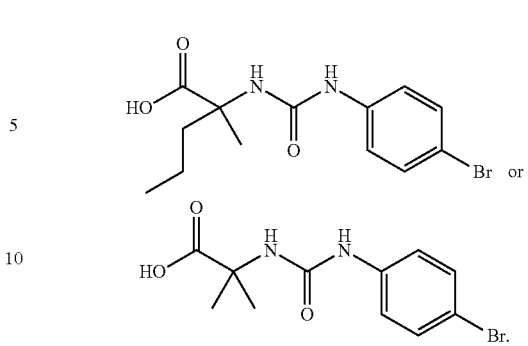

or

In another aspect, the invention provides a compound represented by Formula III or enantiomers, diastereoisomers, tautomers, hydrates, solvates, zwitterions or a pharmaceutically acceptable salt thereof:

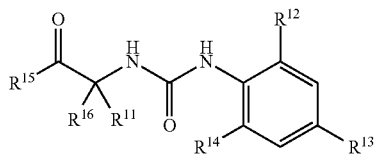

Formula III wherein:
$R^{11}$ is $C_1$-$C_6$ alkyl;
$R^{12}$ is H;
$R^{13}$ is Br;
$R^{14}$ is H;
$R^{15}$ is OH or $NH_2$;
$R^{16}$ is $C_1$-$C_6$ alkyl; and
excluding structures or enantiomers, diastereoisomers, tautomers, hydrates, solvates, zwitterions or a pharmaceutically acceptable salt thereof:

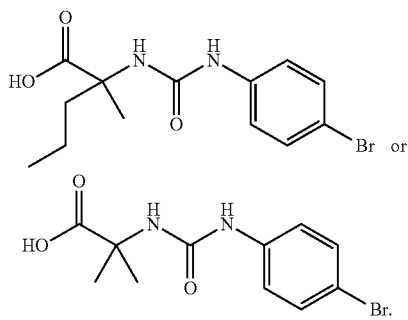

In another aspect, the invention provides a compound represented by Formula III, wherein:
$R^{11}$ is $C_1$-$C_6$ alkyl;
$R^{12}$ is H;
$R^{13}$ is Br;
$R^{14}$ is H;
$R^{15}$ is OH;
$R^{16}$ is $C_1$-$C_6$ alkyl; and
excluding structures or enantiomers, diastereoisomers, tautomers, hydrates, solvates, zwitterions or a pharmaceutically acceptable salt thereof:

In another aspect, the invention provides a compound represented by Formula III, wherein:
$R^{11}$ is $C_1$-$C_6$ alkyl;
$R^{12}$ is H;
$R^{13}$ is Br;
$R^{14}$ is H;
$R^{15}$ is $NH_2$;
$R^{16}$ is $C_1$-$C_6$ alkyl.

The term "alkyl", as used herein, refers to saturated, monovalent or divalent hydrocarbon moieties having linear or branched moieties or combinations thereof and containing 1 to 6 carbon atoms, unless otherwise specified. One methylene (—$CH_2$—) group of the alkyl can be replaced by oxygen, sulfur, sulfoxide, nitrogen, carbonyl, carboxyl, sulfonyl, amide, sulfonamide, by a divalent $C_{4-8}$ cycloalkyl, by a divalent heterocycle, or by a divalent aryl group. Alkyl groups can be independently substituted by halogen atoms, hydroxyl groups, $C_{4-8}$ cycloalkyl groups, amino groups, heterocyclic groups, carboxylic acid groups, phosphonic acid groups, sulphonic acid groups, phosphoric acid groups, nitro groups, amide groups, sulfonamides groups, —C(O)($C_{1-6}$ alkyl) groups, —NH($C_{1-6}$ alkyl) groups, —N($C_{1-6}$ alkyl)($C_{1-6}$ alkyl) groups.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by alkyl groups.

The term "alkynyl", as used herein, refers to a monovalent or divalent hydrocarbon radical having 2 to 6 carbon atoms, derived from a saturated alkyl, having at least one triple bond. Alkynyl groups can be substituted by alkyl groups.

The term "halogen", as used herein, refers to an atom of chlorine, bromine, fluorine, iodine.

The term "cycloalkyl", as used herein, refers to a monovalent or divalent group of 4 to 8 carbon atoms derived from a saturated cyclic hydrocarbon. Cycloalkyl groups can be monocyclic or polycyclic. Cycloalkyl can be independently substituted by halogen atoms, sulfonyl($C_{1-6}$ alkyl) groups, sulfoxide($C_{1-6}$ alkyl) groups, sulfonamide groups, nitro groups, cyano groups, —O($C_{1-6}$ alkyl) groups, —S($C_{1-6}$ alkyl) groups, —$C_{1-6}$ alkyl groups, —$C_{2-6}$ alkenyl groups, —$C_{2-6}$ alkynyl groups, —C(O)($C_{1-6}$ alkyl) groups, —NH($C_{1-6}$ alkyl) groups, —N($C_{1-6}$ alkyl)($C_{1-6}$ alkyl) groups, amino groups, aryl groups, $C_{4-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl can be independently substituted by halogen, sulfonyl($C_{1-6}$ alkyl) groups, —C(O)($C_{1-6}$ alkyl)

groups, sulfonamide groups, amide groups, nitro groups, cyano groups, —O($C_{1-6}$ alkyl)groups, —S($C_{1-6}$ alkyl) groups, —$C_{1-6}$ alkyl groups, —$C_{2-6}$ alkenyl groups, —$C_{2-6}$ alkynyl groups, amino groups, —NH($C_{1-6}$ alkyl) groups, —N($C_{1-6}$ alkyl)($C_{1-6}$ alkyl)groups, $C_{4-8}$ cycloalkyl groups or hydroxyl groups.

The term "aryl" as used herein, refers to an organic moiety derived from an aromatic hydrocarbon consisting of a ring containing 6 to 10 carbon atoms. One or more hydrogen atoms can be substituted by halogen atoms, sulfonyl($C_{1-6}$ alkyl) groups, sulfoxide($C_{1-6}$ alkyl) groups, sulfonamide groups, carboxylic acid groups, —C(O)O($C_{1-6}$ alkyl groups, amide groups, nitro groups, cyano groups, —O($C_{1-6}$ alkyl) groups, —S$C_{1-6}$ alkyl groups, —$C_{1-6}$ alkyl groups, —$C_{2-6}$ alkenyl groups, —$C_{2-6}$ alkynyl groups, aldehyde groups, —C(O)($C_{1-6}$ alkyl) groups, —NH$C_{1-6}$ alkyl groups, —N($C_{1-6}$ alkyl) ($C_{1-6}$ alkyl) groups, amino groups, aryl groups, $C_{4-8}$ cycloalkyl groups or hydroxyl groups. Aryls can be monocyclic or polycyclic.

The term "heterocycle" as used herein, refers to a 3 to 10 membered ring, which can be aromatic or non-aromatic, saturated or unsaturated, containing at least one heteroatom selected from O or N or S or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen, sulfonyl($C_{1-6}$ alkyl) groups, sulfonamide groups, amide groups, nitro groups, cyano groups, —O($C_{1-6}$ alkyl) groups, —S($C_{1-6}$ alkyl) groups, —$C_{1-6}$ alkyl groups, —$C_{2-6}$ alkenyl groups, —$C_{2-6}$ alkynyl groups, amino groups, —C(O)($C_{1-6}$ alkyl) groups, —NH($C_{1-6}$ alkyl) groups, —N($C_{1-6}$ alkyl) ($C_{1-6}$ alkyl) groups, $C_{4-8}$ cycloalkyl groups or hydroxyl groups.

The term "amino" as used herein, represents a group of formula "—$NH_2$".

The term "aldehydes" as used herein, represents a group of formula "—C(O)H".

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "sulfonyl" as used herein, represents a group of formula "—$SO_2^-$".

The term "sulfate" as used herein, represents a group of formula "—O—$S(O)_2$—O—".

The term "nitro" as used herein, represents a group of formula "—$NO_2$".

The term "cyano" or "nitrile" as used herein, represents a group of formula "—CN".

The term "amide" as used herein, represents a group of formula "—NHC(O)—".

The term "sulfonamide" as used herein, represents a group of formula "—$NHS(O)_2$—".

The term "sulfoxide" as used herein, represents a group of formula "—S(O)—".

The term "carboxylic acid" as used herein, represents a group of formula "—C(O)ON".

The term "phosphoric acid" as used herein, represents a group of formula "—(O)$P(O)(OH)_2$".

The term "sulphonic acid" as used herein, represents a group of formula "—$S(O)_2OH$".

The term "phosphonic acid" as used herein, represents a group of formula "—$P(O)(OH)_2$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Compounds of the invention are:

(2S)-2-({[(4-Bromo-2-fluorophenyl)amino]carbonyl}amino)-3-phenyl propanoic acid;

(2S)-2-({[(4-Bromo-2-methylphenyl)amino]carbonyl}amino)-3-phenylpropanoic acid;

(2S)-2-({[(4-Bromo-2,6-difluorophenyl)amino]carbonyl}amino)-3-phenylpropanoic acid;

(2S)-2-({[(4-Bromo-2,6-dimethylphenyl)amino]carbonyl}amino)-3-phenylpropanoic acid;

(2S)-2-({[(2,4-Dichlorophenyl)amino]carbonyl}amino)-3-phenylpropanoic acid;

(2R)-2-({[(4-Bromo-2-fluorophenyl)amino]carbonyl}amino)-3-phenylpropanoic acid;

(2S,3S)-2-({[(4-Bromo-2-fluorophenyl)amino]carbonyl}amino)-3-methylpentanoic acid;

(2S)-({[(4-Bromo-2-fluorophenyl)amino]carbonyl}amino)(phenyl)acetic acid;

(2S)-2-({[(4-Bromophenyl)amino]carbonyl}amino)pentanoic acid;

(2S)-2-[({[4-(Methylthio)phenyl]amino}carbonyl)amino]-3-phenylpropanoic acid;

(2R)-2-[({[4-(methylthio)phenyl]amino}carbonyl)amino]-3-phenylpropanoic acid;

2-({[(4-Bromophenyl)amino]carbonyl}amino)-3-pyridin-2-ylpropanoic acid;

2-({[(4-Bromo-2-fluorophenyl)amino]carbonyl}amino)-3-pyridin-2-ylpropanoic acid;

3-Phenyl-2-{[(pyridin-4-ylamino)carbonyl]amino}propanoic acid;

2-({[(4-Bromo-2-fluorophenyl)amino]carbonyl}amino)-3-(1H-indol-3-yl)propanoic acid;

2-({[(6-Bromoquinazolin-2-yl)amino]carbonyl}amino)-3-phenylpropanoic acid;

(2S)-2-({[(4-Bromo-1-naphthyl)amino]carbonyl}amino)-3-phenylpropanoic acid;

(2S)-4-Methyl-2-{[({4-[(trifluoromethyl)thio]phenyl}amino)carbonyl]amino}pentanoic acid;

(2S)-2-({[(4-Bromophenyl)amino]carbonyl}amino)-4-(methylthio)butanoic acid;

2-({[(4-Bromophenyl)amino]carbonyl}amino)-2,4-dimethylpentanoic acid;

2-({[(4-Bromophenyl)amino]carbonyl}amino)-2-ethylbutanoic acid;

(2S)-4-Methyl-2-[({[4-(trifluoromethyl)phenyl]amino}carbonyl)amino]pentanoic acid;

(2S)-2-{[(4-Bromo-2-fluorophenyl)carbamoyl]amino}pentanoic acid;

2-({[(4-Bromophenyl)amino]carbonyl}amino)-4-(methylthio)butanoic acid;

3-Phenyl-2-({[4-(trifluoromethyl)phenyl]carbamoyl}amino)propanoic acid;

(2S)-2-({[(4-Bromophenyl)amino]carbonyl}amino)-3-phenylpropanamide;

(2S)-2-({[(4-Bromo-2-fluorophenyl)amino]carbonyl}amino)-4-methylpentanamide;

(2S)-2-({[(4-Bromophenyl)amino]carbonyl}amino)-4-methylpentanamide;

(2S,3S)-2-({[(4-Bromo-2-fluorophenyl)amino]carbonyl}amino)-3-methylpentanamide;

(2S)-2-({[(4-Bromo-2-fluorophenyl)amino]carbonyl}amino)pentanamide;

(2S)-2-{[(4-Bromophenyl)carbamoyl]amino}pentanamide.

Some compounds of Formula I, Formula II or Formula III and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I, Formula II or Formula III are able to form.

The acid addition salt form of a compound of Formula I, Formula II or Formula III, that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I, Formula II or Formula III that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I, Formula II or Formula III and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor.

Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor like-1 receptor modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I, Formula II or Formula III. The compounds of Formula I, Formula II or Formula III, according to the invention can be prepared analogously to conventional methods as understood by the person skilled in the art of synthetic organic chemistry. Synthetic Scheme 1 set forth below, illustrates how the compounds according to the invention can be made.

The following abbreviations are used in the general synthetic scheme and in the specific examples:
DCM or $CH_2Cl_2$ methylene chloride
TEA or $Et_3N$ triethylamine
MPLC medium pressure liquid chromatography
EtOAc ethyl acetate
$Na_2SO_4$ sodium sulfate
$CDCl_3$ deuterated chloroform
LiOH lithium hydroxide
MeOH methanol
$CD_3OD$ deuterated methanol
$HCO_2H$ formic acid
$ClCO_2Et$ ethylchloroformate

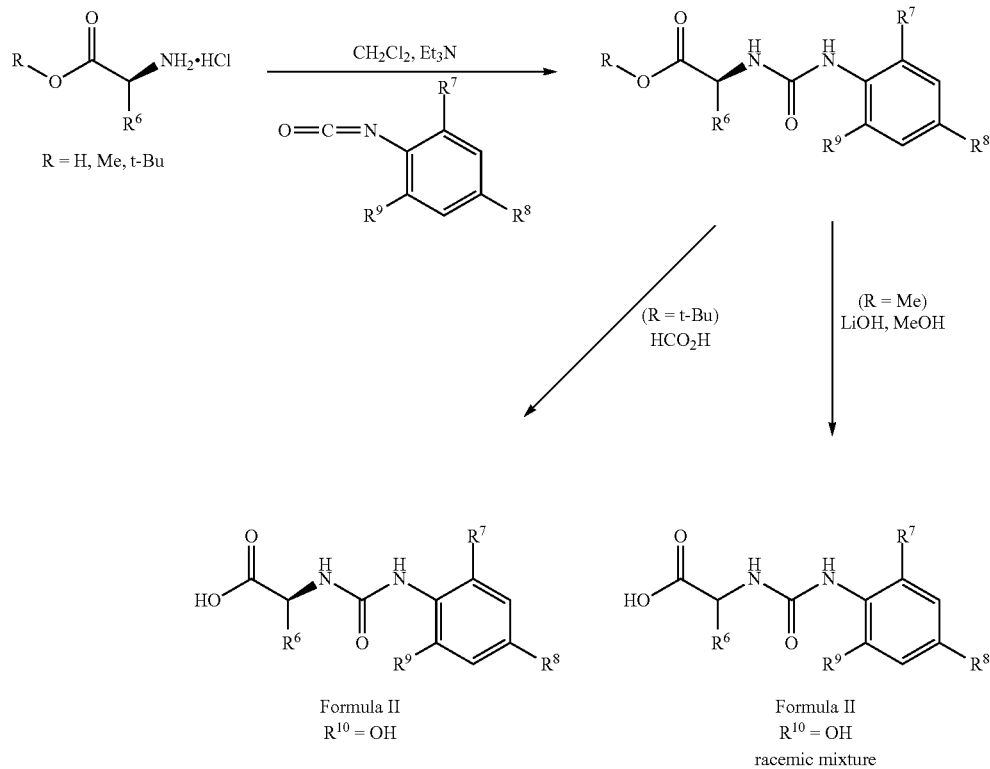

Compounds within the scope of the invention may be prepared as depicted in Scheme 1. To L-phenyl-alanine methyl ester hydrochloride or tert-butyl-L-phenylalanine hydrochloride (100 mg, 0.41 mmol) in methylene chloride at 25° C. was added the desired substituted phenyl isocyanate and triethylamine. The resulting mixture was stirred at 25° C. for 30 minutes. The mixture was concentrated and the residue was purified by medium pressure liquid chromatography on silica gel using ethyl acetate:hexane (1:1) to yield the corresponding alkyl carboxylate compound. The methyl carboxylate, obtained from L-phenyl-alanine methyl ester hydrochloride, was dissolved in methanol and tetrahydrofuran at 25° C. and 2M lithium hydroxide was added. The resulting mixture was stirred at 25° C. for 2 hours. The mixture was concentrated and the residue was acidified with 10% HCl to pH=3, followed by extraction with ethyl acetate. The layers were separated, and the organic layer was washed with water, brine, dried over sodium sulfate, filtered, and concentrated under reduced pressure. The residue was rinsed several times with methylene chloride:hexane (1:1) to yield the racemized carboxylic acid of Formula II as a white solid.

The tert-butyl carboxylate, obtained from tert-butyl-L-phenylalanine hydrochloride, was stirred in formic acid at 25° C. for 3 hours and then quenched with water, extracted with ethyl acetate, washed with water, brine, dried over sodium sulfate, filtered, and concentrated under reduced pressure. The residue was rinsed several times with methylene chloride:hexane to yield the carboxylic acid of Formula II as a white solid.

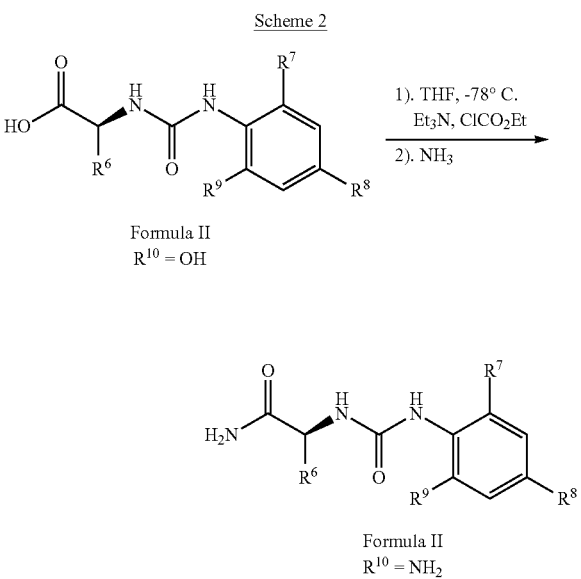

Chiral amino acid ureas of Formula II can be prepared according to Scheme 2. The carboxylic acid derivative of Formula II may be reacted with ethyl chloroformate, followed by ammonia to produce a primary amide derivative or by other methods known to those skilled in the art.

Scheme 3

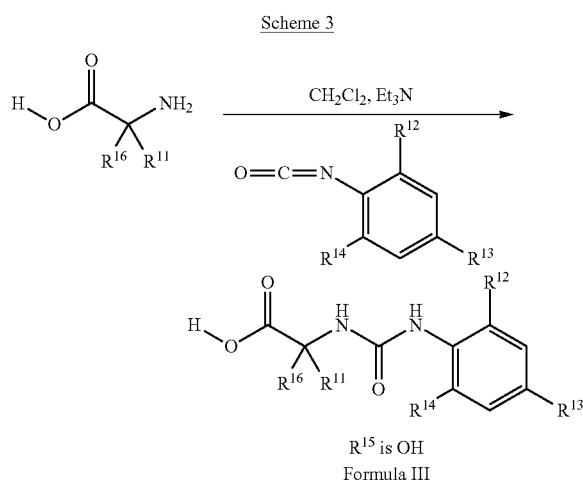

$R^{15}$ is OH
Formula III

Compounds of Formula III can be prepared according to Scheme 3. The amino acid is reacted with a substituted phenylisocyanate to produce a phenylurea derivative as shown in Formula III.

Details of certain specific chemical transformations are provided in the examples.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 12.0; and Intermediates and reagent names used in the examples were generated with softwares such as Chem Bio Draw Ultra version 12.0, ACD version 12.0 or Auto Nom 2000 from MDL ISIS Draw 2.5 SP1.

In general, characterization of the compounds is performed using NMR spectra which were recorded on 300 and/or 600 MHz Varian and acquired at room temperature. Chemical shifts are given in ppm referenced either to internal TMS or to the solvent signal. All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following synthetic schemes illustrate how compounds according to the invention can be made. Those skilled in the art will be routinely able to modify and/or adapt the following schemes to synthesize any compound of the invention covered by Formula II or Formula III.

EXAMPLE 1

Intermediate 1

Methyl (2R)-2-[({[4-(Methylthio)phenyl]amino}carbonynl)amino]-3-phenylpropanoate

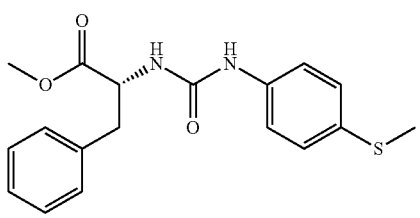

To a solution of D-phenyl-alanine methyl ester hydrochloride (100 mg, 0.46 mmol) and 6 mL of DCM at 25° C. was added 4-methylthio-phenyl isocyanate (72 mg, 0.46 mmol) and TEA (47 mg, 0.69 mmol). The resulting mixture was stirred at 25° C. for 30 minutes. The mixture was concentrated and the residue was purified by MPLC on silica gel using EtOAc:hexanes (25:75) to yield Intermediate 1 as a white solid.

$^1H$ NMR (CDCl$_3$, 300 MHz) δ 7.23-7.34 (m, 3H), 7.06-7.22 (m, 6H), 6.33 (br. s., NH), 4.82 (t, J=6.0 Hz, 1H), 3.75 (s, 3H), 3.13 (ddd, J=19.0 Hz, J=6.0 Hz, 2H).

Intermediates 2 through 24 were prepared from the appropriate amino acid ester hydrochloride salts in the presence of anhydrous methylene chloride and the appropriate isocyanate in a similar manner to the procedure described in Example 1 for Intermediate 1. These intermediates were obtained as white solids, their characteristics are tabulated below in Table 1.

TABLE 1

| Interm. No. | IUPAC name | $^1$H NMR δ (ppm) |
|---|---|---|
| 2 | Methyl (2S)-2-[({[4-(methylthio)phenyl]amino}carbonyl)amino]-3-phenylpropanoate | $^1$H NMR (CDCl$_3$, 300 MHz) δ: 7.22-7.35 (m, 3H), 7.06-7.22 (m, 6H), 4.82 (t, J = 5.7 Hz, 1H), 3.74 (s, 3H), 3.12 (ddd, J = 19.0 Hz, J = 6.0 Hz, 2H), 2.46 (s, 3H). |
| 3 | Methyl (2S)-2-({[(4-bromo-2-fluorophenyl)amino]carbonyl}amino)-3-(1H-indol-3-yl)propanoate | $^1$H NMR (CDCl$_3$, 300 MHz) δ: 8.27 (t, J = 8.8 Hz, 1H), 8.17 (br. s., NH), 7.54 (d, J = 7.9 Hz, 1H), 7.24-7.42 (m, 3H), 7.18 (d, J = 2.3 Hz, NH), 7.05-7.13 (m, 1H), 6.96-7.04 (m, 1H), 6.54 (d, J = 7.9 Hz, NH), 4.81 (dt, J = 8.0, 5.8 Hz, 1H), 3.67 (s, 3H), 3.30 (dd, 2H). |
| 4 | tert-Butyl (2S)-2-({[(4-bromo-2-methylphenyl)amino]carbonyl}amino)-3-phenylpropanoate | $^1$H NMR (CDCl$_3$, 300 MHz) δ: 7.18-7.30 (m, 6H), 7.06-7.14 (m, 2H), 6.20 (br. s., 1H), 4.68 (t, J = 6.0 Hz, 1H), 2.97 (ddd, J = 19.0 Hz, J = 6.0 Hz, 2H), 2.17 (s, 3H), 1.40 (s, 9H). |
| 5 | tert-Butyl (2S)-2-({[(4-bromo-2,6-difluorophenyl)amino]carbonyl}amino)-3-phenylpropanoate | $^1$H NMR (CDCl$_3$, 300 MHz) δ: 7.20-7.33 (m, 3H), 7.07-7.19 (m, 4H), 5.92 (br. s., 1H), 4.62-4.72 (m, 1H), 3.11 (d, J = 5.3 Hz, 2H), 1.41 (s, 9H). |
| 6 | tert-Butyl (2S)-2-({[(4-bromo-2,6-dimethylphenyl)amino]carbonyl}amino)-3-phenylpropanoate | $^1$H NMR (CDCl$_3$, 300 MHz) δ: 7.17-7.25 (m, 5H), 6.96-7.09 (m, 2H), 5.70 (br. s., 1H), 4.54-4.68 (m, 1H), 2.85 (ddd, J = 19.0 Hz, J = 6.0 Hz, 2H), 2.15 (s, 6H), 1.40 (s, 9H). |

TABLE 1-continued

| Interm. No. | IUPAC name | $^1$H NMR δ (ppm) |
|---|---|---|
| 7 | tert-Butyl (2S)-2-({[(2,4-dichlorophenyl)amino]carbonyl}amino)-3-phenylpropanoate | $^1$H NMR (CDCl$_3$, 300 MHz) δ: 8.01 (d, J = 9.1 Hz, 1H), 7.10-7.35 (m, 7H), 6.74 (s, NH), 5.43 (br. s., NH), 4.64 (m, 1H), 3.01 (m, 2H), 1.44 (s, 9H). |
| 8 | tert-Butyl (2R)-2-({[(4-bromo-2-fluorophenyl)amino]carbonyl}amino)-3-phenylpropanoate | $^1$H NMR (CDCl$_3$, 300 MHz) δ: 7.87 (t, J = 8.8 Hz, 1H), 7.22-7.35 (m, 3H), 7.08-7.23 (m, 4H), 6.57 (br. s., NH), 4.71 (t, J = 6.0 Hz, 1H), 2.97 (ddd, J = 19.0 Hz, J = 6.0 Hz, 2H), 1.45 (s, 9H). |
| 9 | tert-Butyl (2S,3S)-2-({[(4-bromo-2-fluorophenyl)amino]carbonyl}amino)-3-methylpentanoate | $^1$H NMR (CDCl$_3$, 300 MHz) δ: 7.92 (t, J = 8.8 Hz, 1H), 7.09-7.22 (m, 4H), 6.66 (s., NH), 4.46 (d, J = 3.5 Hz, 1H), 1.92 (dt, J = 7.0, 4.5 Hz, 1H), 1.37-1.46 (m, 1H), 1.11-1.31 (m, 1H), 0.97 (s, 3H), 0.94 (s, 3H). |
| 10 | tert-Butyl (2S)-({[(4-bromo-2-fluorophenyl)amino]carbonyl}amino)(phenyl)acetate | $^1$H NMR (CDCl$_3$, 300 MHz) δ: 7.96 (t, J = 8.8 Hz, 1H), 7.28-7.42 (m, 5H), 7.12-7.23 (m, 2H), 6.63 (br. s., NH), 5.43 (s, NH), 1.40 (s, 9H). |
| 11 | tert-Butyl (2S)-2-({[(4-Bromophenyl)amino]carbonyl}amino)-3-phenylpropanoate | $^1$H NMR (CDCl$_3$, 300 MHz) δ: 7.20-7.35 (m, 5H), 7.13-7.20 (m, 2H), 7.01-7.10 (m, 2H), 6.79 (br. s., NH), 5.52 (br. s., NH), 4.70 (t, J = 6.2 Hz, 1H), 2.91 (ddd, J = 19.0 Hz, J = 6.0 Hz, 2H), 1.47 (m, 9H). |

TABLE 1-continued

| Interm. No. | IUPAC name | $^1$H NMR δ (ppm) |
|---|---|---|
| 12 | tert-Butyl (2S)-2-({[(4-bromophenyl)amino]carbonyl}amino)pentanoate | $^1$H NMR (CDCl$_3$, 300 MHz) δ: 7.26-7.36 (m, 2H), 7.09-7.18 (m, 2H), 6.95 (br. s., NH), 4.40-4.50 (m, 1H), 1.73-1.89 (m, 1H), 1.52-1.72 (m, 1H), 1.25-1.46 (m, 2H), 0.95 (t, 2H). |
| 13 | tert-Butyl (2S)-4-methyl-2-{[({4-[(trifluoromethyl)thio]phenyl}amino)carbonyl]amino}pentanoate | $^1$H NMR (CD$_3$OD, 300 MHz) δ: 7.53-7.57 (m, 2H), 7.47-7.51 (m, 2H), 4.26 (dd, J = 8.9, 5.7 Hz, 1H), 1.74 (td, J = 13.6, 6.7 Hz, 1H), 1.51-1.65 (m, 2H), 1.47 (s, 9H), 0.97 (t, J = 6.7 Hz, 6H). |
| 14 | tert-Butyl (2S)-4-methyl-2-[({[4-(trifluoromethyl)phenyl]amino}carbonyl)amino]pentanoate | $^1$H NMR (CD$_3$OD, 300 MHz) δ: 7.50 (s, 4H), 4.27 (dd, J = 9.1, 5.6 Hz, 1H), 1.68-1.86 (m, 1H), 1.52-1.66 (m, 2H), 1.45-1.50 (s, 9H), 0.95 (t, J = 6.9 Hz, 6H). |
| 15 | Methyl (2R)-2-({[(4-bromophenyl)amino]carbonyl}amino)-3-pyridin-2-ylpropanoate | 1H NMR (CDCl$_3$, 300 MHz) δ: 8.40 (d, J = 5.0 Hz, 1H), 7.65 (td, J = 7.8, 1.8 Hz, 1H), 7.33-7.40 (m, 2H), 7.15-7.24 (m, 4H), 6.98 (s, NH), 6.66 (d, J = 7.6 Hz, NH), 4.92 (dt, J = 7.8, 5.5 Hz, 1H), 3.69 (s, 3H), 3.34 (dd, 2H). |
| 16 | Methyl (2R)-2-({[(4-bromo-2-fluorophenyl)amino]carbonyl}amino)-3-pyridin-2-ylpropanoate | $^1$H NMR (CDCl$_3$, 300 MHz) δ: 8.44 (d, J = 4.4 Hz, 1H), 7.92-8.02 (m, 1H), 7.65 (td, J = 7.7, 1.9 Hz, 1H), 7.15-7.23 (m, 5H), 6.92 (br. s., NH), 6.73 (d, J = 7.9 Hz, NH), 4.94 (dt, J = 8.0, 5.4 Hz, 1H), 3.70 (s, 3H), 3.28-3.44 (m, 2H). |

TABLE 1-continued

| Interm. No. | IUPAC name | $^1$H NMR δ (ppm) |
|---|---|---|
| 17 | Methyl (2S)-3-phenyl-2-{[(pyridin-4-ylamino)carbonyl]amino}propanoate | $^1$H NMR (CDCl$_3$, 300 MHz) δ: 8.58 (br. s., NH), 8.20 (d, J = 6.4 Hz, 2H), 7.17-7.27 (m, 5H), 7.08 (dd, J = 7.3, 1.8 Hz, 2H), 6.04 (d, J = 7.9 Hz, NH), 4.76-4.88 (m, 1H), 3.74 (s, 3H), 2.92 (ddd, J = 19.0 Hz, J = 6.0 Hz, 2H). |
| 18 | Methyl (2S)-2-({[(6-bromoquinazolin-2-yl)amino]carbonyl}amino)-3-phenylpropanoate | $^1$H NMR (acetone-d$_6$, 300 MHz) δ: 9.36 (s, 1H), 8.26 (d, J = 1.8 Hz, NH), 8.02 (dd, J = 8.9, 2.2 Hz, 1H), 7.56 (d, J = 9.1 Hz, 1H), 7.21-7.35 (m, 5H), 4.81-4.90 (m, 1H), 3.74 (s, 3H), 3.26 (d, 2H). |
| 19 | tert-Butyl (2S)-2-({[(4-bromo-2-fluorophenyl)amino]carbonyl}amino)-3-phenylpropanoate | $^1$H NMR (CDCl$_3$, 300 MHz) δ: 7.85-7.94 (m, 1H), 7.12-7.34 (m, 7H), 6.50 (d, J = 2.1 Hz, NH), 4.66-4.74 (m, 1H), 3.09 (t, J = 5.6 Hz, 2H), 1.44 (s, 9H). |
| 20 | tert-Butyl (2S)-2-({[(4-bromo-1-naphthyl)amino]carbonyl}amino)-3-phenylpropanoate | $^1$H NMR (CDCl$_3$, 300 MHz) δ: 8.23-8.33 (m, 1H), 8.01 (d, J = 8.5 Hz, 1H), 7.49-7.76 (m, 3H), 7.33 (d, J = 7.9 Hz, 1H), 7.10-7.21 (m, 3H), 6.93-7.07 (m, 2H), 6.75 (br. s., 1H), 4.72 (t, J = 6.2 Hz, 1H), 2.91 (ddd, J = 19.0 Hz, J = 6.0 Hz, 2H), 1.36 (s, 9H). |
| 21 | tert-Butyl (2S)-4-methyl-2-[({[4-(trifluoromethyl)phenyl]amino}carbonyl)amino]pentanoate | $^1$H NMR (CD$_3$OD, 300 MHz) δ: 7.50 (s, 4H), 4.27 (dd, J = 9.1, 5.6 Hz, 1H), 1.68-1.86 (m, 1H), 1.52-1.66 (m, 2H), 1.45-1.50 (s, 9H), 0.95 (t, J = 6.9 Hz, 6H). |

TABLE 1-continued

| Interm. No. | IUPAC name | ¹H NMR δ (ppm) |
|---|---|---|
| 22 | tert-Butyl (2S)-2-{[(4-bromo-2-fluorophenyl)carbamoyl]amino}pentanoate | ¹H NMR (CDCl₃, 300 MHz) δ: 7.92 (t, J = 8.6 Hz, 1H), 7.09-7.21 (m, 2H), 6.71 (d, J = 3.2 Hz, NH), 4.39-4.49 (m, 1H), 1.74-1.90 (m, 1H), 1.55-1.71 (m, 1H), 1.47-1.54 (m, 9H), 1.27-1.47 (m, 2H), 0.91-1.01 (m, 3H). |
| 23 | Methyl (2S)-3-phenyl-2-[({[4-(trifluoromethyl)phenyl]amino}carbonyl)amino]propanoate | ¹H NMR (CDCl₃, 300 MHz) δ: 7.42 (d, J = 8.5 Hz, 2H), 7.21-7.35 (m, 5H), 7.08-7.16 (m, 2H), 6.79 (br. s., 1H), 5.40 (br. s., 1H), 4.84 (br. s, 1H), 3.80 (s, 3H), 3.09 (ddd, J = 19.0 Hz, J = 6.0 Hz, 2H). |
| 24 | Methyl (2S)-({[(4-bromophenyl)amino]carbonyl}amino)-4-(methylthio)butanoate | ¹H NMR (CDCl₃, 300 MHz) δ: 7.35-7.43 (m, 2H), 7.16-7.24 (m, 2H), 4.68 (dd, J = 7.6, 5.0 Hz, 1H), 3.78 (s, 3H), 2.52-2.62 (m, 2H), 2.12-2.26 (m, 1H), 2.10 (s, 3H), 1.92-2.06 (m, 1H). |

EXAMPLE 2

Compound 1

(2S)-2-({[(4-Bromo-2-fluorophenyl)amino]carbonyl}amino)-3-phenylpropanoic acid

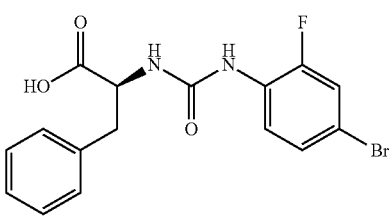 [SMILES: Cc1cc(Br)ccc1NC(=O)N[C@@H](Cc1ccccc1)C(=O)O]

A solution of Intermediate 19 (50 mg, 0.12 mmol) and 0.5 mL of formic acid was stirred at 25° C. for 3 hours. The resulting reaction was quenched with water (1 mL), and the product was extracted with EtOAc. The organic layer was washed with water, brine, dried over Na₂SO₄, filtered, and concentrated under reduced pressure. The residue was rinsed four times with DCM:hexanes (1:1) to yield Compound 1 as a white solid.

¹H NMR (acetone-d₆, 300 MHz) δ: 8.26 (t, J=8.9 Hz, 1H), 8.18 (br. s., NH), 7.18-7.37 (m, 7H), 6.47 (d, J=8.5 Hz, NH), 4.75 (q, J=6.5 Hz, 1H), 3.18 (ddd, J=19.0 Hz, J=6.0 Hz, 2H).

Compounds 2 through 16 were prepared from the corresponding intermediate in a similar manner to the procedure described in Example 2 for Compound 1. The intermediate used and the compound's characteristics are tabulated below in Table 2.

TABLE 2

| Comp. No. | IUPAC name | Interm. No. | ¹H NMR δ (ppm) for compound |
|---|---|---|---|
| 2 | (2S)-2-({[(4-Bromo-2-methylphenyl)amino]carbonyl}amino)-3-phenylpropanoic acid | 4 | ¹H NMR (acetone-$d_6$, 300 MHz) δ: 7.92 (d, J = 8.5 Hz, 2H), 7.61 (br. s., 1H), 7.19-7.32 (m, 7H), 6.32 (d, J = 9.1 Hz, 1H), 4.75 (dt, J = 7.9, 5.9 Hz, 1H), 3.18 (ddd, J = 19.0 Hz, J = 6.0 Hz, 2H), 2.20 (s, 3H). |
| 3 | (2S)-2-({[(4-Bromo-2,6-difluorophenyl)amino]carbonyl}amino)-3-phenylpropanoic acid | 5 | ¹H NMR (acetone-$d_6$, 300 MHz) δ: 7.66 (s, NH), 7.18-7.35 (m, 7H), 6.26 (d, J = 8.8 Hz, NH), 4.62-4.74 (m, 1H), 3.04 (ddd, J = 19.0 Hz, J = 6.0 Hz, 2H), 2.20 (s, 3H). |
| 4 | (2S)-2-({[(4-Bromo-2,6-dimethylphenyl)amino]carbonyl}amino)-3-phenylpropanoic acid | 6 | ¹H NMR (acetone-$d_6$, 300 MHz) δ: 7.16-7.33 (m, 7H), 4.61-4.72 (m, 1H), 2.98 (ddd, J = 19.0 Hz, J = 6.0 Hz, 2H), 2.18 (s, 6H). |
| 5 | (2S)-2-({[(2,4-Dichlorophenyl)amino]carbonyl}amino)-3-phenylpropanoic acid | 7 | ¹H NMR (acetone-$d_6$, 300 MHz) δ: 8.33 (d, J = 9.1 Hz, 1H), 8.01 (s, NH), 7.42 (d, J = 2.3 Hz, 1H), 7.17-7.35 (m, 6H), 6.78 (d, J = 7.9 Hz, 1H), 4.70 (m, 1H), 3.01 (ddd, J = 19.0 Hz, J = 6.0 Hz, 2H). |
| 6 | (2R)-2-({[(4-Bromo-2-fluorophenyl)amino]carbonyl}amino)-3-phenylpropanoic acid | 8 | ¹H NMR (acetone-$d_6$, 300 MHz) δ: 8.26 (t, J = 8.6 Hz, 1H), 8.19 (br. s., NH), 7.16-7.40 (m, 7H), 6.48 (d, J = 10.3 Hz, 1H), 4.68-4.84 (m, 1H), 3.04 (ddd, J = 19.0 Hz, J = 6.0 Hz, 2H). |

TABLE 2-continued

| Comp. No. | IUPAC name | Interm. No. | $^1$H NMR δ (ppm) for compound |
|---|---|---|---|
| 7 | (2S,3S)-2-({[(4-Bromo-2-fluorophenyl)amino]carbonyl}amino)-3-methylpentanoic acid | 9 | $^1$H NMR (acetone-$d_6$, 300 MHz) δ: 8.29 (t, J = 8.8 Hz, 1H), 8.14 (br. s., NH), 7.23-7.41 (m, 2H), 6.57 (d, J = 8.5 Hz, NH), 4.46 (dd, J = 8.6. 4.5 Hz, 1H), 1.86-2.02 (m, 1H), 1.44-1.61 (m, 1H), 1.16-1.37 (m, 1H), 0.89-1.04 (m, 6H). |
| 8 | (2S)-({[(4-Bromo-2-fluorophenyl)amino]carbonyl}amino)(phenyl)acetic acid | 10 | $^1$H NMR (acetone-$d_6$, 300 MHz) δ: 8.26 (t, J = 8.9 Hz, 1H), 7.46-7.53 (m, 1H), 7.30-7.44 (m, 4H), 7.27 (dt, J = 8.9, 1.8 Hz, 1H), 7.15 (d, J = 6.4 Hz, 1H), 5.49 (d, 1H). |
| 9 | (2S)-2-({[(4-Bromophenyl)amino]carbonyl}amino)pentanoic acid | 12 | $^1$H NMR (acetone-$d_6$, 300 MHz) δ: 8.20 (s, NH), 7.43-7.52 (m, 2H), 7.33-7.41 (m, 2H), 6.08 (d, J = 9.1 Hz, NH), 4.38-4.50 (m, 1H), 1.77-1.92 (m, 1H), 1.61-1.76 (m, 1H), 1.36-1.53 (m, 2H), 0.89-1.00 (m, 3H). |
| 10 | (2S)-2-({[(4-Bromo-1-naphthyl)amino]carbonyl}amino)-3-phenylpropanoic acid | 20 | $^1$H NMR (acetone-$d_6$, 300 MHz) δ: 8.47 (s, NH), 8.11-8.25 (m, 2H), 8.04 (d, J = 8.5 Hz, NH), 7.78 (d, J = 8.5 Hz, 1H), 7.54-7.71 (m, 2H), 7.22-7.35 (m, 5H), 6.50 (d, J = 6.2 Hz, 1H), 4.75-4.88 (m, 1H), 3.07 (ddd, J = 19.0 Hz, J = 6.0 Hz, 2H). |
| 11 | (2S)-4-Methyl-2-{[({4-[(trifluoromethyl)thio]phenyl}amino)carbonyl]amino}pentanoic acid | 13 | $^1$H NMR (CD$_3$OD, 300 MHz) δ: 7.52-7.58 (m, 2H), 7.47-7.52 (m, 2H), 4.37 (dd, J = 9.4, 5.0 Hz, 1H), 1.70-1.82 (m, 1H), 1.53-1.69 (m, 2H), 0.99 (d, J = 3.2 Hz, 3H), 0.97 (d, J = 3.2 Hz, 3H). |
| 12 | (2S)-4-Methyl-2-[({[4-(trifluoromethyl)phenyl]amino}carbonyl)amino]pentanoic acid | 21 | $^1$H NMR (CD$_3$OD, 300 MHz) δ: 7.49-7.57 (m, 4H), 4.38 (dd, J = 9.4, 5.0 Hz, 1H), 1.69-1.87 (m, 1H), 1.51-1.69 (m, 2H), 0.92-1.01 (m, 6H). |

TABLE 2-continued

| Comp. No. | IUPAC name | Interm. No. | $^1$H NMR δ (ppm) for compound |
|---|---|---|---|
| 13 | (2S)-2-{[(4-Bromo-2-fluorophenyl)carbamoyl]amino}pentanoic acid 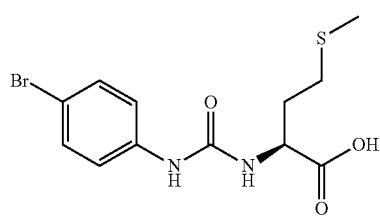 | 22 | $^1$H NMR (acetone-$d_6$, 300 MHz) δ: 8.27 (t, J = 8.9 Hz, 1H), 8.08 (br. s., NH), 7.34 (dd, J = 10.8, 2.3 Hz, 1H), 7.28 (dt, J = 8.9, 1.7 Hz, 1H), 6.56 (d, J = 7.9 Hz, NH), 4.45 (td, J = 7.8, 5.1 Hz, 1H), 1.79-1.93 (m, 1H), 1.64-1.77 (m, 1H), 1.37-1.53 (m, 2H), 0.91-1.00 (m, 3H). |

EXAMPLE 3

Compound 14

(2S)-2-({[(4-Bromophenyl)amino]carbonyl}amino)-4-(methylthio)butanoic acid

To a solution of L-methionine (CAS 59-51-8) in DCM at 25° C. was added 4-bromophenylisocyate and TEA. The resulting mixture was stirred at 25° C. for 12 hours. The mixture was concentrated and the residue was purified by MPLC on silica gel using methanol: dichloromethane (40 : 60) to yield Compound 14.

$^1$H NMR (CD$_3$OD, 300 MHz) δ: 7.23-7.41 (m, 4H), 4.31-4.42 (m, 1 H), 2.56 (d, J 15.5 Hz, 2H), 2.12-2.23 (m, 1H), 2.08 (s, 3H), 1.98 (dt, J=14.0, 7.2 Hz, 1H).

EXAMPLE 4

Compound 15

(2S)-2-[({[4-(Methylthio)phenyl]amino}carbonyl)amino]-3-phenylpropanoic acid

A solution of Intermediate 2 (25 mg, 0.07 mmol), acetonitrile (0.3 mL), phosphate buffer pH=7.2 (8 mL) and 7 ku of esterase from rabbit liver was stirred vigorously at 25° C. for 48 hours. The resulting reaction was diluted with acetonitrile and concentrated under reduced pressure to dryness. The residue was rinsed three times with DCM:hexanes (1:4) then acetone to yield Compound 15 as a white solid.

$^1$H NMR (acetone-$d_6$, 300 MHz) δ: 8.16 (br. s., NH), 7.37-7.49 (m, 2H), 7.14-7.34 (m, 7H), 5.90 (d, J=7.3 Hz, 1H), 4.66-4.80 (m, 1H), 3.15 (ddd, J=19.0 Hz, J=6.0 Hz, 2H).

Compounds 16 through 23 were prepared from the corresponding intermediate in a similar manner to the procedure described in Example 2 for Compound 1 using lithium hydroxide and methanol instead of formic acid. The intermediate used and the compound's characteristics are tabulated below in Table 3.

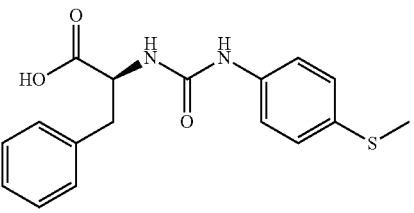 [SMILES: CSc1ccc(NC(=O)N[C@@H](Cc2ccccc2)C(=O)O)cc1]

TABLE 3

| Comp. No. | IUPAC name | Interm. No. | $^1$H NMR δ (ppm) for compound |
|---|---|---|---|
| 16 | 2-({[(4-Bromophenyl)amino]carbonyl}amino)-3-pyridin-2-ylpropanoic acid | 15 | $^1$H NMR (acetone-$d_6$, 300 MHz) δ: 8.72 (d, J = 5.6 Hz, 1H), 8.65 (s, NH), 8.36 (td, J = 7.9, 1.8 Hz, 1H), 7.97 (d, J = 7.9 Hz, 1H), 7.81 (ddd, J = 7.5, 5.8, 1.3 Hz, 1H), 7.31-7.41 (m, 4H), 7.09 (d, J = 7.3 Hz, NH), 4.88 (td, J = 8.6, 4.2 Hz, 1H), 3.73 (dd, J = 14.4, 4.4 Hz, 1H), 3.49 (dd, 1H). |

TABLE 3-continued

| Comp. No. | IUPAC name | Interm. No. | ¹H NMR δ (ppm) for compound |
|---|---|---|---|
| 17 | 2-({[(4-Bromo-2-fluorophenyl)amino]carbonyl}amino)-3-pyridin-2-ylpropanoic acid | 16 | ¹H NMR (acetone-$d_6$, 300 MHz) δ: 8.79 (d, J = 5.6 Hz, 1H), 8.54 (td, J = 7.8, 1.6 Hz, 1H), 8.32 (br. s., 1H), 8.15 (d, J = 8.2 Hz, 1H), 7.94-8.05 (m, 2H), 7.76 (d, J = 10.0 Hz, NH), 7.32 (dd, J = 10.7, 2.2 Hz, 1H), 7.14-7.26 (m, 1H), 4.87-5.02 (m, 1H), 3.89 (dd, J = 13.9, 3.4 Hz, 1H), 3.50 (dd, 1H). |
| 18 | 3-Phenyl-2-{[(pyridin-4-ylamino)carbonyl]amino}propanoic acid | 17 | ¹H NMR (CD$_3$OD, 300 MHz) δ: 8.44 (d, J = 6.4 Hz, 2H), 8.02 (d, J = 6.4 Hz, NH), 7.89 (d, J = 6.7 Hz, 2H), 7.14-7.34 (m, 5H), 6.85 (d, J = 6.4 Hz, 2H), 4.61-4.70 (m, 1H), 3.02-3.26 (m, 2H). |
| 19 | 2-({[(4-Bromo-2-fluorophenyl)amino]carbonyl}amino)-3-(1H-indol-3-yl)propanoic acid | 3 | ¹H NMR (acetone-$d_6$, 300 MHz) δ: 8.29 (t, J = 8.6 Hz, 1H), 8.19 (br. s., MH), 7.60 (d, J = 7.9 Hz, 1H), 7.24-7.41 (m, 3H), 7.20 (d, J = 2.3 Hz, NH), 7.04-7.12 (m, 1H), 6.94-7.02 (m, 1H), 6.52 (d, J = 7.6 Hz, NH), 4.81 (dt, J = 7.8, 5.6 Hz, 1H), 3.25-3.45 (m, 2H). |
| 20 | 2-({[(6-Bromoquinazolin-2-yl)amino]carbonyl}amino)-3-phenylpropanoic acid | 18 | ¹H NMR (CDCl$_3$, 300 MHz) δ: 9.35 (s, 1H), 8.26 (d, J = 2.1 Hz, NH), 8.01 (dd, J = 8.9, 2.2 Hz, 1H), 7.55 (d, J = 8.8 Hz, 1H), 7.33-7.41 (m, 2H), 7.19-7.32 (m, 3H), 4.83-4.92 (m, 1H), 3.31 (dd, 2H). |
| 21 | 2-({[(4-Bromophenyl)amino]carbonyl}amino)-4-(methylthio)butanoic acid | 24 | ¹H NMR (CD$_3$OD, 300 MHz) δ: 7.23-7.41 (m, 4H), 4.31-4.42 (m, 1H), 2.56 (d, J = 15.5 Hz, 2H), 2.12-2.23 (m, 1H), 2.08 (s, 3H), 1.98 (dt, J = 14.0, 7.2 Hz, 1H). |

TABLE 3-continued

| Comp. No. | IUPAC name | Interm. No. | $^1$H NMR δ (ppm) for compound |
|---|---|---|---|
| 22 | 3-Phenyl-2-({[4-(trifluoromethyl)phenyl]carbamoyl}amino)propanoic acid | 23 | $^1$H NMR (acetone-$d_6$, 300 MHz) δ: 8.53 (br. s., 1H), 7.62-7.72 (m, 2H), 7.51-7.61 (m, 2H), 7.16-7.36 (m, 5H), 6.07 (d, J = 7.9 Hz, 1H), 4.70-4.82 (m, 1H), 3.18 (ddd, J = 19.0 Hz, J = 6.0 Hz, 2H). |
| 23 | 2-[({[4-(Methylthio)phenyl]amino}carbonyl)amino]-3-phenylpropanoic acid | 1 | $^1$H NMR (acetone-$d_6$, 300 MHz) δ: 8.16 (br. s., NH), 7.37-7.49 (m, 2H), 7.14-7.34 (m, 7H), 5.90 (d, J = 7.3 Hz, 1H), 4.66-4.80 (m, 1H), 3.15 (ddd, J = 19.0 Hz, J = 6.0 Hz, 2H). |

EXAMPLE 5

Compound 24

2-({[(4-Bromophenyl)amino]carbonyl}amino)-2,4-dimethylpentanoic acid

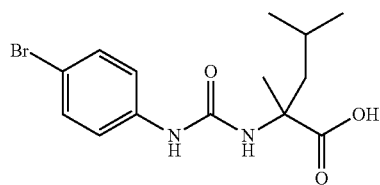 [SMILES: CC(C)CC(C)(NC(=O)Nc1ccc(Br)cc1)C(=O)O]

Compound 24 was prepared according to Scheme 3. 2-methyl-leucine (CAS 144-24-1) was reacted with a 4-bromophenylisocyanate (CAS 2493-0-9).

$^1$H NMR (CD$_3$OD, 300 MHz) δ: 7.31-7.39 (m, 2H), 7.22-7.30 (m, 2H), 1.80-1.92 (m, 2H), 1.71-1.82 (m, 1H), 1.56-1.67 (m, 2H), 1.44 (s, 3H), 0.98 (d, J=1.2 Hz, 3H), 0.95 (d, J=1.2 Hz, 3H).

Compound 25 was prepared from 2-amino-2-ethyl-butanoic acid (CAS 2566-29-2) in a similar manner to the procedure described in Example 3 for Compound 24. The compound's characteristics are tabulated below in Table 4.

TABLE 4

| 25 | 2-({[(4-Bromophenyl)amino]carbonyl}amino)-2-ethylbutanoic acid | $^1$H NMR (acetone-$d_6$, 300 MHz) δ: 8.76 (br. s., 1H), 7.44-7.52 (m, 2H), 7.31-7.40 (m, 2H), 6.30 (br. s., 1H), 2.29-2.48 (m, 2H), 1.75-1.92 (m, 2H), 0.76-0.86 (m, 6H). |
|---|---|---|

EXAMPLE 6

Compound 26

(2S)-2-({[(4-Bromophenyl)amino]carbonyl}amino)-3-phenylpropanamide

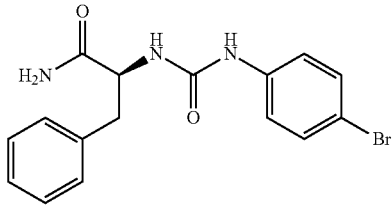 [SMILES: NC(=O)[C@H](Cc1ccccc1)NC(=O)Nc1ccc(Br)cc1]

To a solution of N-[[(4-bromophenyl)amino]carbonyl]-L-Phenylalanine (CAS 111183-53-0) (50 mg, 0.14 mmol) and 5 mL of anhydrous tetrahydrofuran under argon at −78° C. was added triethylamine (19 mg, 0.18 mmol), and ethyl chloroformate (19 mg, 0.17 mmol). The mixture was stirred at −78° C. for 30 minutes, and ammonia gas was bubbled into reaction flask for 1 minutes. The resulting mixture was stirred at 25° C. for 2 hours. The mixture was quenched with water (1 mL), and the products were extracted with ethyl acetate (20 mL). The layers were separated, and the organic layer was washed with water, and brine, and dried over $Na_2SO_4$, and filtered, and concentrated under reduced pressure. The resulting product was purified by preparative thin layer chromatography on silica gel using an eluent of ethyl acetate:hexane (75:25) to yield Compound 26, as an off white solid.

$^1$H NMR (acetone-$d_6$, 300 MHz) δ: 8.27 (s, NH), 7.39-7.47 (m, 2H), 7.31-7.39 (m, 2H), 7.14-7.29 (m, 5H), 7.09 (br. s., NH), 6.51 (br. s., NH), 6.07 (d, J=7.9 Hz, NH), 4.60-4.70 (m, 1H), 3.10-3.20 (m, 1H), 2.93-3.05 (m, 1H).

Compounds 27 through 31 were prepared from the corresponding compound or starting material in a similar manner to the procedure described in Example 5 for Compound 26. The intermediate used and the compound's characteristics are tabulated below in Table 5.

TABLE 5

| Comp. No. | IUPAC name | Comp. No. or Starting materials | $^1$H NMR δ (ppm) for compound |
|---|---|---|---|
| 27 | (2S)-2-({[(4-Bromo-2-fluorophenyl)amino]carbonyl}amino)-4-methylpentanamide | N-[[(4-bromo-2-fluorophenyl)amino]carbonyl]-L-Leucine CAS 1308957-63-2 | $^1$H NMR (acetone-$d_6$, 300 MHz) δ: 8.28 (t, J = 8.9 Hz, 1H), 8.07 (br. s., NH), 7.33 (dd, J = 10.8, 2.3 Hz, 1H), 7.23-7.30 (m, 1H), 7.10 (br. s., NH), 6.50 (d, J = 8.2 Hz, NH), 6.38 (br. s., NH), 4.42 (ddd, J = 9.6, 8.3, 5.0 Hz, 1H), 1.70-1.87 (m, 1H), 1.59-1.70 (m, 1H), 1.44-1.59 (m, 1H), 0.95 (d, J = 1.5 Hz, 3H), 0.93 (d, 3H). |
| 28 | (2S)-2-({[(4-Bromophenyl)amino]carbonyl}amino)-4-methylpentanamide | N-[[(4-bromophenyl)amino]carbonyl]-L-Leucine CAS 11183-45-0 | $^1$H NMR (acetone-$d_6$, 300 MHz) δ: 8.17 (s, NH), 7.41-7.50 (m, 2H), 7.33-7.40 (m, 2H), 6.03 (d, J = 8.2 Hz, NH), 4.39 (ddd, J = 9.4, 8.2, 5.0 Hz, 1H), 3.58 (q, J = 5.6 Hz, 2H), 3.26-3.37 (m, 2H), 1.66-1.81 (m, 1H), 1.44-1.67 (m, 2H), 0.94 (d, J = 1.5 Hz, 3H), 0.92 (d, J = 1.4 Hz, 3H). |
| 29 | (2S,3S)-2-({[(4-Bromo-2-fluorophenyl)amino]carbonyl}amino)-3-methylpentanamide | 7 | $^1$H NMR (CD$_3$OD, 300 MHz) δ: 7.99 (t, J = 8.8 Hz, 1H), 7.31 (dd, J = 10.7, 2.2 Hz, 1H), 7.19-7.27 (m, 1H), 4.18 (d, J = 6.2 Hz, 1H), 1.78-1.95 (m, 1H), 1.49-1.65 (m, 1H), 1.10-1.27 (m, 1H), 1.00 (d, J = 6.7 Hz, 3H), 0.91-0.98 (m, 3H). |

TABLE 5-continued

| Comp. No. | IUPAC name | Comp. No. or Starting materials | $^1$H NMR δ (ppm) for compound |
|---|---|---|---|
| 30 | (2S)-2-({[(4-Bromo-2-fluorophenyl)amino]carbonyl}amino)pentanamide | 16 | $^1$H NMR (acetone-$d_6$, 300 MHz) δ: 8.28 (t, J = 8.8 Hz, 1H), 8.12 (br. s., NH), 7.33 (dd, J = 11.0, 2.2 Hz, 1H), 7.26 (dt, J = 8.9, 1.9 Hz, 1H), 7.07 (br. s., NH), 6.55 (d, J = 7.0 Hz, NH), 6.40 (br. s., NH), 4.38 (td, J = 7.8, 5.3 Hz, 1H), 1.73-1.89 (m, 1H), 1.54-1.70 (m, 1H), 1.24-1.49 (m, 2H), 0.92 (t, J = 7.3 Hz, 3H). |
| 31 | (2S)-2-{[(4-Bromophenyl)carbamoyl]amino}pentanamide | 9 | $^1$H NMR (acetone-$d_6$, 300 MHz) δ: 8.23 (s, NH), 7.43-7.52 (m, 2H), 7.32-7.41 (m, 2H), 7.06 (s, NH), 6.41 (br. s., NH), 6.07 (d, J = 8.5 Hz, NH), 4.37 (td, J = 7.7, 5.1 Hz, 1H), 1.72-1.86 (m, 1H), 1.53-1.69 (m, 1H), 1.40 (dq, J = 15.2, 7.4 Hz, 2H), 0.91 (t, J = 7.3 Hz, 3H). |

Biological Data

Biological activity of compounds according to Formulae II and III is set forth in Table 6 below. CHO-Ga16 cells stably expressing FPRL1 were cultured in (F12, 10% FBS, 1% PSA, 400 μg/ml geneticin and 50 μg/ml hygromycin) and HEK-Gqi5 cells stable expressing FPR1 were cultured in (DMEM high glucose, 10% FBS, 1% PSA, 400 μg/ml geneticin and 50 μg/ml hygromycin). In general, the day before the experiment, 18,000 cells/well were placed in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as $EC_{50}$ (nM) and efficacy values.

TABLE 6

| IUPAC Name Compound | FPRL-1 Ga16-CHO $EC_{50}$ (nM) (Rel. eff.) |
|---|---|
| (2S)-2-({[(4-Bromophenyl)amino]carbonyl}amino)-4-(methylsulfanyl)butanoic acid | 75 (1.00) |
| (2S)-4-Methyl-2-[({4-[(trifluoromethyl)sulfanyl]phenyl}aminocarbonyl)amino]pentanoic acid | 2377 (0.64) |
| (2S)-4-Methyl-2-({[4-(trifluoromethyl)phenyl] aminocarbonyl}amino)pentanoic acid | 29 (0.94) |
| 2-{[(4-Bromophenyl) aminocarbonyl]amino}-2-ethylbutanoic acid | 24 (1.03) |
| 2-{[(4-Bromophenyl) aminocarbonyl]amino}-2,4-dimethylpentanoic acid | 16 (0.95) |
| (2S)-2-{[(4-Bromo-2-fluorophenyl) aminocarbonyl]amino}-4-methylpentanamide | 120 (1.13) |
| (2S)-2-{[(4-Bromophenyl) aminocarbonyl]amino}-4-methylpentanamide | 48 (0.91) |
| (2S)-2-{[(4-Bromo-2-fluorophenyl) aminocarbonyl]amino}pentanamide | 56 (1.07) |
| (2S)-2-{[(4-Bromophenyl)carbamoyl]amino}pentanamide | 109 (0.97) |
| 2-{[(4-Bromophenyl) aminocarbonyl]amino}-4-(methylsulfanyl)butanoic acid | 93 (0.94) |
| (2S,3S)-2-{[(4-Bromo-2-fluorophenyl) aminocarbonyl]amino}-3-methylpentanamide | 241 (0.78) |
| (2S)-2-{[(4-Bromophenyl) aminocarbonyl]amino}-3-phenylpropanamide | 47 (1.02) |
| 2-{[(4-Bromo-2-fluorophenyl) aminocarbonyl]amino}-3-(1H-indol-3-yl)propanoic acid | 120 (1.04) |
| 2-({[(6-Bromoquinazolin-2-yl)amino]carbonyl}amino)-3-phenylpropanoic acid | ND (0.25) |

TABLE 6-continued

| IUPAC Name Compound | FPRL-1 Gal6-CHO EC$_{50}$ (nM) (Rel. eff.) |
|---|---|
| (2S)-{[(4-Bromo-2-fluorophenyl) aminocarbonyl]amino}(phenyl)ethanoic acid | 88 (1.02) |
| (2S,3S)-2-{[(4-Bromo-2-fluorophenyl) aminocarbonyl]amino}-3-methylpentanoic acid | 8 (0.89) |
| (2R)-2-{[(4-Bromo-2-fluorophenyl) aminocarbonyl]amino}-3-phenylpropanoic acid | 1713 (0.96) |
| (2S)-2-{[(4-Bromo-2-fluorophenyl) aminocarbonyl]amino}-3-phenylpropanoic acid | 51 (0.88) |
| (2S)-2-({[4-(Methylsulfanyl)phenyl] aminocarbonyl}amino)-3-phenylpropanoic acid | 77 (0.87) |
| 2-({[4-(Methylsulfanyl)phenyl] aminocarbonyl}amino)-3-phenylpropanoic acid | 169 (0.76) |
| (2S)-3-Phenyl-2-({[4-(trifluoromethyl)phenyl] aminocarbonyl}amino)propanoic acid | 91 (1.05) |
| (2R)-2-({[(4-Bromo-2-fluorophenyl)amino]carbonyl}amino)-3-phenylpropanoic acid | 30 (1.0) |
| (2S)-2-({[(4-Bromo-2-methylphenyl)amino]carbonyl}amino)-3-phenylpropanoic acid | 1553 (1.0) |
| (2S)-2-({[(4-Bromo-2,6-difluorophenyl)amino]carbonyl}amino)-3-phenylpropanoic acid | 563 (1.0) |
| (2S)-2-({[(4-Bromo-2,6-dimethylphenyl)amino]carbonyl}amino)-3-phenylpropanoic acid | 2396 (0.82) |
| (2S)-2-({[(4-Bromo-1-naphthyl)amino]carbonyl}amino)-3-phenylpropanoic acid | 5097 (0.53) |
| (2S)-2-({[(2,4-Dichlorophenyl)amino]carbonyl}amino)-3-phenylpropanoic acid | 1149 (1.0) |
| 2-({[(4-Bromophenyl)amino]carbonyl}amino)-3-pyridin-2-ylpropanoic acid | 488 (1.0) |
| 2-({[(4-Bromo-2-fluorophenyl)amino]carbonyl}amino)-3-pyridin-2-ylpropanoic acid | 713 (1.0) |
| (2S)-2-{[(4-Bromophenyl) aminocarbonyl]amino}-3-phenylpropanamide | 29 (1.0) |

What is claimed is:

1. A compound represented by Formula II, its enantiomers, diastereoisomers, tautomers, or a pharmaceutically acceptable salt thereof:

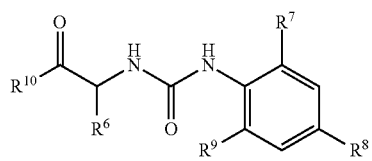

Formula II wherein:
$R^6$ is —CH$_2$—(C$_{6-10}$)aryl or —CH$_2$-heterocycle wherein one or more hydrogen atoms of the aryl group can be substituted by halogen atoms, sulfonyl(C$_{1-6}$ alkyl) groups, sulfoxide(C$_{1-6}$ alkyl) groups, sulfonamide groups, carboxylic acid groups, —C(O)O(C$_{1-6}$ alkyl) groups, amide groups, nitro groups, cyano groups, —O(C$_{1-6}$ alkyl)groups, —S(C$_{1-6}$ alkyl) groups, —C$_{1-6}$ alkyl groups, —C$_{2-6}$ alkenyl groups, —C$_{2-6}$ alkynyl groups, aldehyde groups, —C(O)(C$_{1-6}$ alkyl) groups, —NH(C$_{1-6}$ alkyl)groups, —N(C$_{1-6}$ alkyl)(C$_{1-6}$ alkyl) groups, amino groups, C$_{4-8}$ cycloalkyl groups or hydroxyl groups,
wherein the heterocycle contains at least one heteroatom selected from O or N interrupting the carbocyclic ring structure;
$R^7$ is H, F or methyl;
$R^8$ is Br or F;
$R^9$ is H, F or methyl;
$R^{10}$ is OH or NH$_2$; and
excluding structures or enantiomers, diastereoisomers, tautomers or a pharmaceutically acceptable salt thereof:

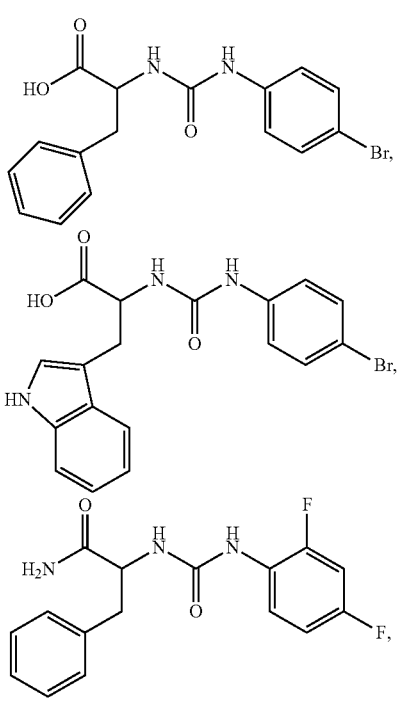

-continued

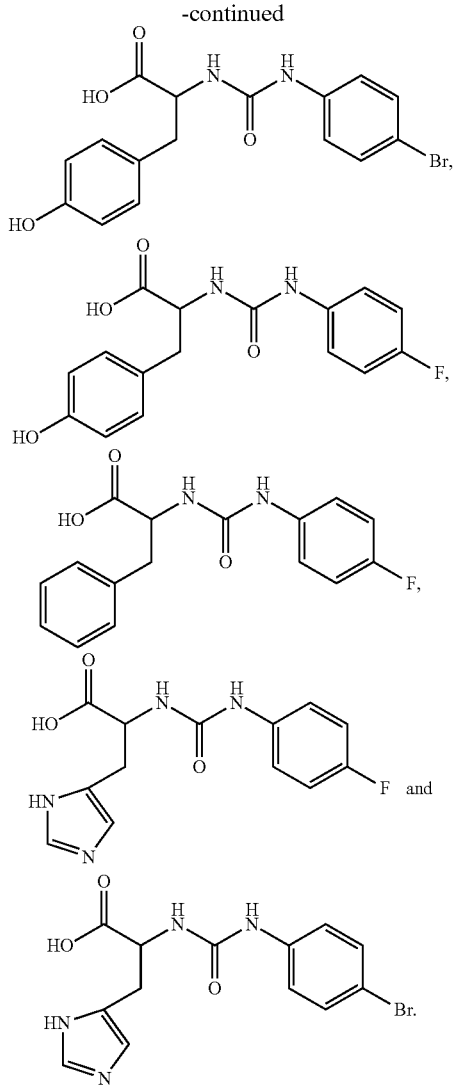

2. A compound according to claim 1, wherein:
$R^8$ is Br.

3. A compound according to claim 1, wherein:
$R^6$ is —$CH_2$—$(C_{6-10})$aryl.

4. A compound according to claim 1, wherein:
$R^6$ is —$CH_2$-heterocycle.

5. A compound according to claim 1, wherein:
$R^{10}$ is OH.

6. A compound according to claim 1, wherein:
$R^{10}$ is $NH_2$.

7. A compound according to claim 1, wherein:
$R^7$ is H;
$R^8$ is Br; and
$R^9$ is H.

8. A compound according to claim 1, wherein the compound is selected from:
  (2S)-2-({[(4-Bromo-2-fluorophenyl)amino]carbonyl}amino)-3-phenylpropanoic acid;
  (2S)-2-({[(4-Bromo-2-methylphenyl)amino]carbonyl}amino)-3-phenylpropanoic acid;
  (2S)-2-({[(4-Bromo-2,6-difluorophenyl)amino]carbonyl}amino)-3-phenylpropanoic acid;
  (2S)-2-({[(4-Bromo-2,6-dimethylphenyl)amino]carbonyl}amino)-3-phenylpropanoic acid;
  (2R)-2-({[(4-Bromo-2-fluorophenyl)amino]carbonyl}amino)-3-phenylpropanoic acid;
  2-({[(4-bromophenyl)amino]carbonyl}amino)-3-pyridin-2-ylpropanoic acid;
  2-({[(4-bromo-2-fluorophenyl)amino]carbonyl}amino)-3-pyridin-2-ylpropanoic acid;
  2-({[(4-bromo-2-fluorophenyl)amino]carbonyl}amino)-3-(1H-indol-3-yl)propanoic acid; and
  (2S)-2-({[(4-bromophenyl)amino]carbonyl}amino)-3-phenylpropanamide.

\* \* \* \* \*